(12) United States Patent
Reddy et al.

(10) Patent No.: US 6,548,553 B2
(45) Date of Patent: Apr. 15, 2003

(54) STYRYL SULFONE ANTICANCER AGENTS

(75) Inventors: E. Premkumar Reddy, Villanova, PA (US); M. V. Ramana Reddy, Upper Darby, PA (US)

(73) Assignee: Temple University-of the Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 09/919,061

(22) Filed: Jul. 31, 2001

(65) Prior Publication Data

US 2002/0022666 A1 Feb. 21, 2002

Related U.S. Application Data

(63) Continuation-in-part of application No. 09/509,227, filed as application No. PCT/US98/20580 on Oct. 1, 1998, now Pat. No. 6,359,013.
(60) Provisional application No. 60/060,933, filed on Oct. 3, 1997.

(51) Int. Cl.[7] ............................................... A61K 31/10
(52) U.S. Cl. ....................................... 514/710; 514/709
(58) Field of Search .................................. 514/709, 710

(56) References Cited

U.S. PATENT DOCUMENTS

| | | | |
|---|---|---|---|
| 2,532,612 A | 12/1950 | Doumani | 260/609 |
| 3,185,743 A | 5/1965 | Combe et al. | 260/682 |
| 3,418,101 A | 12/1968 | Buchholtz et al. | 71/72 |
| 3,514,386 A | 5/1970 | Oswald et al. | 204/162 |
| 3,917,714 A | 11/1975 | Richmond | 260/607 A |
| 4,161,407 A | 7/1979 | Campbell | 96/114 |
| 4,386,221 A | 5/1983 | Hyatt et al. | 568/28 |
| 4,937,388 A | 6/1990 | Bushell et al. | 568/56 |
| 5,659,087 A | 8/1997 | Aikins et al. | 568/27 |

FOREIGN PATENT DOCUMENTS

| | | |
|---|---|---|
| WO | WO99/18068 | 4/1999 |
| WO | WO01/26645 | 4/2001 |

OTHER PUBLICATIONS

D. Bhaskar Reddy, N.S. Reddy, S. Reddy, M.V.R. Reddy and S. Balasubramanyam, *Org. Prep. Proc. Int.*, 20(3):205–212 (1988).
D. Bhasker Reddy, P. V. Ramana Reddy, V. Padmavathi, and M.V.R. Reddy, *Sulfur Lett.*, 13(2):83–90 (1991).
M.V.R. Reddy and S. Reddy, *Acta Chim. Acad. Sci. Hung.*, 115(3):269–271 (1984).

(List continued on next page.)

*Primary Examiner*—Jean F. Vollano
(74) *Attorney, Agent, or Firm*—Drinkerrrr Biddle & Reath LLP

(57) ABSTRACT

Styryl sulfone compounds of the invention selectively inhibit proliferation of tumor cells, and induce apoptosis of tumor cells, while sparing normal cells. The compounds, which are useful in the treatment of cancer and other proliferative disorders, have (a) the formula II:

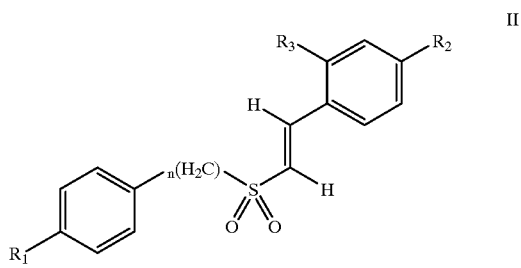

wherein n is zero or one; $R_1$ is selected from the group consisting of hydrogen, chlorine, fluorine and bromine; $R_2$ is selected from the group consisting of hydrogen, chlorine, fluorine, bromine, methyl and methoxy; and $R_3$ is selected from the group consisting of hydrogen, chlorine and fluorine; provided, $R_2$ may not be methyl or methoxy when $R_1$ and $R_3$ are both hydrogen and n is zero or one; and $R_1$, $R_2$ and $R_3$ may not all be hydrogen when n is one;

(b) the formula III:

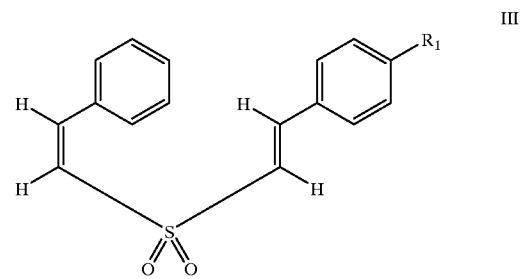

wherein $R_1$ is selected from the group consisting of hydrogen, chlorine, fluorine and bromine; or (c) or the formula IV:

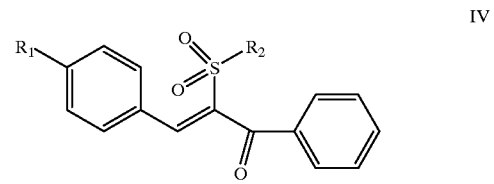

wherein $R_1$ is selected from the group consisting of fluorine and bromine, and $R_2$ is selected from the group consisting of 2-chlorophenyl, 4-chlorophenyl, 4-fluorophenyl and 2-nitrophenyl.

27 Claims, 8 Drawing Sheets

OTHER PUBLICATIONS

M.V.R. Reddy, V. Vijayalakshmi, D. Bhaskar Reddy and P.V. Ramana Reddy, *Phosphorus, Sulfur Silicon Relat. Elem.*, 60:209–214 (1991).

M.V. Reddy and S. Reddy, *Acta Chim. Acad. Sci. Hung.*, 120(4):275–280 (1985).

M.V.R. Reddy and S. Reddy, *Synthesis* No. 4, 322–323 (1984).

M.V.R. Reddy, S. Reddy and D.B. Reddy, *Sulfur Lett.*, 7(2):43–48 (1987).

Reddy et al., "A New Route for the Synthesis of Styrylbenzylsulfones, Precursors of 1–benzylsulfonyl–2–arylcyclopropanes", *Phosphorus, Sulfur, and Silicon*, 53:285–290 (1990).

Mieczyslaw Makosza and Irina Krylova, "Some Reactions of the Chloromethyl *trans–beta*–Styryl Sulfone Carbanion", *Liebigs Ann./Recueil*, pp. 2337–2340 (1997).

Reddy et al., "Phase Transfer Catalysis—a Facile Method for Cyclopropanation of Some Isomeric Styryl Benzyl Sulfones and Bis(styryl)sulfones", *Acta Chim. Hung.*, 131(1):83–92 (1994).

CA:124:175763, abs of Reddy et al., *Indian J. Heterocycl. Chem.*, (May 1995), 5(1), 11–14.

CA:124:146025, abs of Reddy et al., *Indian J. Heterocycl. Chem.* (1995), 4(4), 259–264.

CA:126:166162, Thompson et al. abs of *Cancer Res.*, (Feb. 1997) 57(2), 267–271.

Benati, et al., *J. Org. Chem.*, 59:2818–2823 (1994).

CA:120:323356 abs of Reddy et al., *Sulf. Lett.* (1993), 16(5–6), 227–35.

CA:122:132682 abs of Reddy et al., *Phosphorus, Sulfur Silicon Relat. Elem.* (1994), 90(1–4), 1–10.

CA:124:8731 abs of Reddy et al., *Indian J. Chem. Sect. B: Org. Chem. Incl. Med. Chem.* (1995) 34B(9), 816–22.

CA:76:121420 abs of Findlay et al. *Brit J. Dermatol.*, Suppl. (1971), No. 7, 44–9.

CA:105:133446 abs of Naidu et al., *Proc.—Indian Acad. Sci., Chem. Sci* (1985), 95(4), 391–5.

CA:126:185889 abs of Japanese Pat. App. 09–03,037 (Jan. 7, 1997).

STYRYL SULFONE ANTICANCER AGENTS

CROSS-REFERENCE TO RELATED APPLICATIONS

This is a continuation-in-part of co-pending application Ser. No. 09/509,227, filed Mar. 24, 2000, now U.S. Pat. No. 6,359,013 B1 which is a 371 of international application PCT/US98/20580, filed Oct. 1, 1998, which claims the benefit of provisional application 60/060,933, filed Oct. 3, 1997, abandoned. The entire disclosures of the aforesaid international and provisional applications are incorporated herein by reference.

FIELD OF THE INVENTION

The invention relates to compositions and methods for the treatment of cancer and other proliferative disorders.

BACKGROUND OF THE INVENTION

Extracellular signals received at transmembrane receptors are relayed into the cells by the signal transduction pathways (Pelech et al., Science 257:1335 (1992)) which have been implicated in a wide array of physiological processes such as induction of cell proliferation, differentiation or apoptosis (Davis et al., J. Biol. Chem. 268:14553 (1993)). The Mitogen Activated Protein Kinase (MAPK) cascade is a major signaling system by which cells transduce extracellular cues into intracellular responses (Nishida et al., Trends Biochem. Sci. 18:128 (1993); Blumer et al., Trends Biochem. Sci. 19:236 (1994)). Many steps of this cascade are conserved, and homologous for MAP kinases have been discovered in different species.

In mammalian cells, the Extracellular-Signal-Regulated Kinases (ERKs), ERK-1 and ERK-2 are the archetypal and best-studied members of the MAPK family, which all have the unique feature of being activated by phosphorylation on threonine and tyrosine residues by an upstream dual specificity kinase (Posada et al., Science 255:212 (1992); Biggs III et al., Proc. Natl. Acad. Sci. USA 89:6295 (1992); Garner et al., Genes Dev. 6:1280 (1992)).

Recent studies have identified an additional subgroup of MAPKs, known as c-Jun NH2-terminal kinases 1 and 2 (JNK-1 and JNK-2), that have different substrate specificities and are regulated by different stimuli (Hibi et al., Genes Dev. 7:2135 (1993)). JNKs are members of the class of stress-activated protein kinases (SPKs). JNKs have been shown to be activated by treatment of cells with UV radiation, pro-inflammatory cytokines and environmental stress (Derijard et al., Cell 1025 (1994)). The activated JNK binds to the amino terminus of the c-Jun protein and increases the protein's transcriptional activity by phosphorylating it at ser63 and ser73 (Adler et al., Proc. Natl. Acad. Sci. USA 89:5341 (1992); Kwok et al., Nature 370:223 (1994)).

Analysis of the deduced primary sequence of the JNKs indicates that they are distantly related to ERKs (Davis, Trends Biochem. Sci. 19:470 (1994)). Both ERKs and JNKs are phosphorylated on Tyr and Thr in response to external stimuli resulting in their activation (Davis, Trends Biochem. Sci. 19:470 (1994)). The phosphorylation (Thr and Tyr) sites, which play a critical role in their activation are conserved between ERKs and JNKs (Davis, Trends Biochem. Sci. 19:470 (1994)). However, these sites of phosphorylation are located within distinct dual phosphorylation motifs: Thr-Pro-Tyr (JNK) and Thr-Glu-Tyr (ERK). Phosphorylation of MAPKs and JNKs by an external signal often involves the activation of protein tyrosine kinases (PTKs) (Gille et al., Nature 358:414 (1992)), which constitute a large family of proteins encompassing several growth factor receptors and other signal transducing molecules.

Protein tyrosine kinases are enzymes which catalyze a well defined chemical reaction: the phosphorylation of a tyrosine residue (Hunter et al., Annu Rev Biochem 54:897 (1985)). Receptor tyrosine kinases in particular are attractive targets for drug design since blockers for the substrate domain of these kinases is likely to yield an effective and selective antiproliferative agent. The potential use of protein tyrosine kinase blockers as antiproliferative agents was recognized as early as 1981, when quercetin was suggested as a PTK blocker (Graziani et al., Eur. J. Biochem. 135:583–589 (1983)).

The best understood MAPK pathway involves extracellular signal-regulated kinases which constitute the Ras/Raf/MEK/ERK kinase cascade (Boudewijn et al., Trends Biochem. Sci. 20, 18 (1995)). Once this pathway is activated by different stimuli, MAPK phosphorylates a variety of proteins including several transcription factors which translocate into the nucleus and activate gene transcription. Negative regulation of this pathway could arrest the cascade of these events.

What are needed are new anticancer chemotherapeutic agents which target receptor tyrosine kinases and which arrest the Ras/Raf/MEK/ERK kinase cascade. Oncoproteins in general, and signal transducing proteins in particular, are likely to be more selective targets for chemotherapy because they represent a subclass of proteins whose activities are essential for cell proliferation, and because their activities are greatly amplified in proliferative diseases.

What is also needed are new cell antiproliferative agents, and anticancer therapeutics in particular, which are highly selective in the killing of proliferating cells such as tumor cells, but not normal cells.

SUMMARY OF THE INVENTION

According to one embodiment of the invention, novel compounds are provided according to formula I:

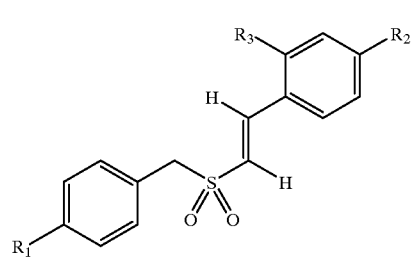

wherein
  $R_1$ and $R_2$ are independently selected from the group consisting of chlorine, fluorine and bromine; and
  $R_3$ is selected from the group consisting of hydrogen and fluorine;
  $R_1$ and $R_2$ may not both be chlorine when $R_3$ is hydrogen; and
  $R_1$ may not be chlorine when $R_2$ is fluorine and $R_3$ is hydrogen in the same compound.

According to another embodiment of the invention, a pharmaceutical composition is provided comprising a pharmaceutically acceptable carrier and a compound of formula II

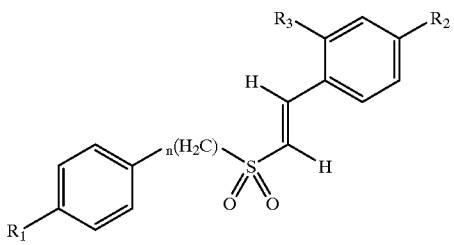

wherein n is zero or one;

$R_1$ is selected from the group consisting of hydrogen, chlorine, fluorine and bromine;

$R_2$ is selected from the group consisting of hydrogen, chlorine, fluorine, bromine, methyl and methoxy; and $R_3$ is selected from the group consisting of hydrogen, chlorine and fluorine; provided, $R_2$ may not be methyl or methoxy when $R_1$ and $R_3$ are both hydrogen and n is zero or one; and $R_1$, $R_2$ and $R_3$ may not all be hydrogen when n is one.

According to a preferred embodiment, the pharmaceutical composition comprises a pharmaceutically acceptable carrier and a compound of the formula II, wherein $R_3$ is hydrogen, and $R_1$ and $R_2$ are independently selected from the group consisting of chlorine, fluorine and bromine.

According to another embodiment of the invention, a pharmaceutical composition is provided comprising a pharmaceutically acceptable carrier and a compound of the formula III

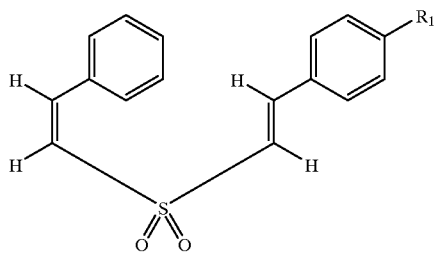

wherein $R_1$ is selected from the group consisting of hydrogen, chlorine, fluorine and bromine.

The invention also relates to a pharmaceutical composition comprising a pharmaceutically acceptable carrier and a compound of the formula IV wherein $R_1$ is selected from the group consisting of fluorine and bromine, and

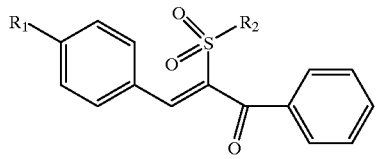

$R_2$ is selected from the group consisting of 2-chlorophenyl, 4-chlorophenyl, 4-fluorophenyl and 2-nitrophenyl.

According to another embodiment of the invention, a method of treating an individual for a proliferative disorder, particularly cancer, is provided comprising administering to said individual an effective amount of a compound according to any of formulae II, III or IV, alone or in combination with a pharmaceutically acceptable carrier. In another embodiment, a method of inhibiting growth of tumor cells in an individual afflicted with cancer is provided, comprising administering to said individual an effective amount of a compound according to formula II, III or IV, alone or in combination with a pharmaceutically acceptable carrier. Furthermore, a method of inducing apoptosis of tumor cells in an individual afflicted with cancer is provided comprising administering to said individual an effective amount of a compound according to formula II, III or IV, alone or in combination with a pharmaceutically acceptable carrier.

According to certain embodiments of the invention, the treatment is for breast or prostate cancer, and the cells whose growth is inhibited are breast or prostate tumor cells. According to another embodiment of the invention, the treatment is for a proliferative disorder, other than breast and prostate cancer, and the cells whose growth is inhibited are other than breast or prostate tumor cells. According to certain embodiments of the invention, the cancers treated are selected from the group consisting of cancers of the ovaries, lung, colon, rectum, brain, kidney, pancreas and skin; leukemias; lymphomas; sarcomas; squamous cell carcinomas and papillomas; basal cell carcinomas and papillomas; and epidermoid cancers. The growth of cancer cells, particularly tumor cells associated with these cancers, is inhibited. The cells are induced to undergo apoptosis.

DETAILED DESCRIPTION OF THE INVENTION

Figure 1A:
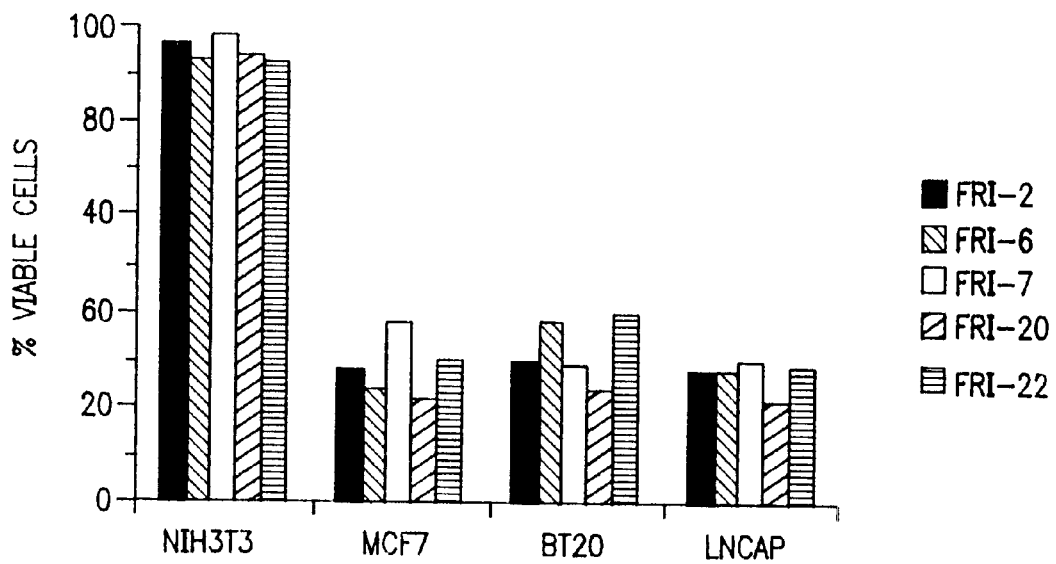
FIGS. 1A and 1B are bar graphs of the effect of compounds E-2,4-difluorostyryl-4-fluorobenzyl sulfone (FRI-2), E-4-fluorostyryl 4-bromobenzyl sulfone (FRI-6), E-4-bromostyryl 4-fluorobenzyl sulfone (FRI-7), E-4-fluorostyryl 4-chlorobenzyl sulfone (FRI-20) and E-4-chlorostyryl 4-chlorobenzyl sulfone (FRI-22) on NIH3T3, MCF7, BT-20 and LnCaP cells. Cells were treated with the compounds at 2.5 $\mu$M (FIG. 1A) or 5.0 $\mu$M (FIG. 1B) concentration and cell viability was determined after 48 hours by Trypan blue exclusion method. Each data point represents the average of three independent experiments. The standard deviation did not exceed 10%.

According to the present invention, certain styryl sulfone derivatives affect the MAPK signal transduction pathway, thereby affecting tumor cell growth and viability. Without wishing to be bound by any theory, it is believed that the compounds affect the MAPK signal transduction pathway, thereby affecting tumor cell growth and viability. This cell growth inhibition is associated with regulation of the ERK and JNK types of MAPK. The compounds selectively kill various tumor cell types without killing normal cells.

The compounds inhibit the growth and proliferation of tumor cells in a dose-dependent manner. This cell growth inhibition is associated with regulation of the ERK and JNK types of MAPK. The ability of the styryl sulfones to regulate these MAPKs and induce cell growth arrest is dictated by the nature and position of the functional groups present in the compound.

Treatment of tumor cells with the styryl sulfone compounds of the invention leads to inhibition of tumor cell proliferation and induction of apoptotic cell death. The effect is observed for estrogen receptor (ER) positive as well as estrogen receptor negative cells, although one breast cancer cell line tested, cell line 361, showed considerable resistance to styryl sulfones. Inhibition of cell proliferation and induction of apoptotic cell death is also observed for androgen-dependent as well as androgen-independent prostate tumor cells, although the former are considerably more sensitive to the styryl sulfones.

Tumor cells treated with the compounds of the invention accumulate in the G2/M phase of the cell cycle. As the cells exit the G2/M phase, they appear to undergo apoptosis. Treatment of normal cells with the styryl sulfones fails to produce a similar effect on cell cycle progression. Treatment of normal cells with the styryl sulfones does not result in apoptosis.

Both cells treated with the styryl sulfone compounds of the invention and untreated cells exhibit similar levels of intracellular ERK-2, but the biochemical activity of ERK-2, as judged by its ability to phosphorylate the substrate myelin basic protein (MBP), is considerably diminished in drug-treated cell compared to untreated cells. In prostate tumor cells, FR-20, a preferred compound of the invention, reduced the phosphorylation status of MBP by more than 80% compared to mock-treated cells. Western blot analysis of the drug and mock-treated cell lysates with ERK-2 antibody shows the same amount of protein in both lysates, indicating that higher levels of phosphorylated MBP in mock treated cells was not due to an unequal quantity of ERK-2 protein in the lysates. Without wishing to be bound by any theory, these results suggest that the styryl sulfones of the present invention block the phosphorylating capacity of ERK-2.

The styryl sulfones of the present invention enhance the ability of JNK to phosphorylate c-Jun protein compared to mock-treated cells. Without wishing to be bound by any theory, this result suggests that the styryl sulfones may be acting like pro-inflammatory cytokines or UV light, activating the JNK pathway, which in turn may switch on genes responsible for cell growth inhibition and apoptosis.

The compounds of the invention have been shown to inhibit the proliferation of tumor cells by inducing cell death. The compounds do not kill normal cells in concentrations at which tumor cells are killed. The compounds are effective against a broad range of tumor types, including but not limited to the following: breast, prostate, ovarian, lung, colorectal, brain (e.g., gliomas, glioblastomas and astrocytomas), renal, pancreatic, lung (small cell and non-small cell), skin (e.g., melanomas) and ovarian. The compounds are also effective against leukemias and lymphomas, particularly Burkets lymphoma and acute lymphocytic lymphoma. The compounds are effective against sarcomas, particularly uterine sarcomas; squamous cell carcinomas and papillomas; basal cell carcinomas and papillomas; and epidermoid cancers;. It is believed that the mechanism of action is not tumor-specific.

The compound are active not only against highly tumorigenic cells, such as breast tumor cells, but also against less tumorigenic cells, and even non-tumorigenic hyperplasias such a Turner Syndrome fibroblasts and benign skin lesions.

The compounds are also believed useful in the treatment of non-cancer proliferative disorders, including but not limited to the following: hemangiomatosis in new born, secondary progressive multiple sclerosis, chronic progressive myelodegenerative disease, neurofibromatosis, ganglioneuromatosis, keloid formation, Pagets Disease of the bone, fibrocystic disease of the breast, Peronies and Duputren's fibrosis, restenosis and cirrhosis.

Treatment of this broad range of tumor cells with the styryl benzylsulfone compounds of the invention leads to inhibition of cell proliferation and induction of apoptotic cell death.

Tumor cells treated with the compounds of the invention accumulate in the G2/M phase of the cell cycle. As the cells exit the G2/M phase, they appear to undergo apoptosis. Treatment of normal cells with the styryl sulfones does not result in apoptosis.

Synthesis of Styryl Sulfones

The compounds of the invention are characterized by cis-trans isomerism resulting from the presence of one or more double bonds. The compounds are named according to the Cahn-Ingold-Prelog system, the IUPAC 1974 Recommendations, Section E: Stereochemistry, in *Nomenclature of Organic Chemistry*, Pergamon, Elmsford, N.Y., 1979 (the "Blue Book"). See also, March, *Advanced Organic Chemistry*, John Wiley & Sons, Inc., New York, N.Y., 4th ed., 1992, p. 127–138. Stearic relations around a double bond are designated as "Z" or "E".

(E)-styryl and benzyl sulfones are prepared by Knoevenagel condensation of aromatic aldehydes with active methylene molecules such as aryl, benzyl, styryl sulfonyl acetic acids, phenacyl aryl sulfones and sulfonyl diacetic acid. The procedure is described by Reddy et al.,*Acta. Chim. Hung* 115:269 (1984); Reddy et al., *Sulfur Letters* 13:83 (1991); Reddy et al.,*Synthesis* 322 (1984); and Reddy et al., *Sulfur Letters* 7:43 (1987), the entire disclosures of which are incorporated herein by reference.

Preparation of Benzylsulfonyl and Arylsulfonyl Acetic Acids

Aryl and benzylsulfonyl acetic acids are the starting compounds for the synthesis of (E)-styryl aryl and (E)-styryl benzyl sulfones. Arylsulfonyl acetic acids may be prepared by the condensation of sodium aryl sulfinate with chloroacetic acid at alkaline pH. An alternate method for the synthesis of same compounds involves oxidizing the products obtained by the condensation of sodium arylthiolate with chloroacetic acid.

Benzylsulfonyl acetic acids may be synthesized by 30% hydrogen peroxide oxidation of the condensation products of the condensation of benzyl chlorides with sodium thioglycollate. Alternatively, benzylsulfonyl acetic acids may be synthesized by 30% hydrogen peroxide oxidation of the products of the condensation of sodium salts of benzyl thiols with chloroacetic acids.

Synthesis of (E)-Styryl Aryl and (E)-Benzyl Sulfones

To prepare the (E)-styryl benzyl and (E)-styryl benzyl sulfones, a mixture of the appropriate sulfonylacetic acid (e.g., 10 mmol), an aromatic aldehyde (e.g., 10 mmol) and a catalytic amount of benzylamine in acetic acid (e.g., 15 ml) is refluxed for 2–3 hours. After cooling, dry ether is added and the reaction mixture is refrigerated overnight. The ethereal solution is washed successively with a saturated solution of sodium hydrogen carbonate, sodium bisulfite, dilute hydrochloric acid and finally with water. Evaporation of the sodium sulfate dried ethereal solution gives solid products of (E)-styryl aryl or benzyl sulfones which may be recrystallized with 2-propanol or 95% ethanol.

Synthesis of (E),(E)- and (E),(Z)-bis(Styryl) Sulfones (E),(E)-bis(styryl) sulfones may be prepared by the condensation of sulfonyl diacetic acid with aromatic aldehydes in the presence of benzylamine as catalyst. The reaction mixture is refluxed for 2 hours in glacial acetic acid. After cooling, absolute ether is added to the reaction mixture, which is washed successively with saturated solution of sodium bicarbonate, sodium bisulfite, dilute hydrochloric acid and water. Evaporation of the dried etherial layer yields (E),(E)-bis(styryl) sulfones.

(Z),(E)-bis(styryl) sulfones may be prepared by mixing a solution of (Z)-styrylsulfonyl acetic acid in glacial acetic acid with araldehyde and benzylamine. The solution is boiled for 3 hours. The reaction mixture is cooled and dry ether is added. Any product separated is filtered. The filtrate is diluted with more ether and washed with saturated solution of sodium hydrogen carbonate, sodium bisulfite, dilute hydrochloric acid and water. The ether layer is separated, dried and evaporated to give (Z),(E)-bis(styryl) sulfones.

Therapeutic Administration

The styryl sulfones of the invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and to deleterious to the recipient.

The compounds of the invention may be administered to individuals (mammals, including animals and humans) afflicted with cancer.

The compounds are also useful in the treatment of non-cancer proliferative disorders, that is, proliferative disorders which are characterized by benign indications. Such disorders may also be known as "cytoproliferative" or "hyperproliferative" in that cells are made by the body at an atypically elevated rate. Such disorders include, but are not limited to, the following: hemangiomatosis in new born, secondary progressive multiple sclerosis, chronic progressive myelodegenerative disease, neurofibromatosis, ganglioneuromatosis, keloid formation, Pagets Disease of the bone, fibrocystic disease of the breast, Peronies and Duputren's fibrosis, restenosis and cirrhosis.

The compounds may be administered by any route, including oral and parenteral administration. Parenteral administration includes, for example, intravenous, intramuscular, intraarterial, intraperitoneal, intranasal, rectal, intravaginal, intravesical (e.g., to the bladder), intradermal, topical or subcutaneous administration. The active agent is preferably administered with a pharmaceutically acceptable carrier selected on the basis of the selected route of administration and standard pharmaceutical practice.

Also contemplated within the scope of the invention is the instillation of drug in the body of the patient in a controlled formulation, with systemic or local release of the drug to occur at a later time. For example, the drug may localized in a depot for controlled release to the circulation, or for release to a local site of tumor growth.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences*, 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil, saline solution, aqueous dextrose (glucose) and related sugar solutions, or a glycol such as propylene glycol or polyethylene glycol. Solutions for parenteral administration preferably contain a water soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The specific dose of compound according to the invention to obtain therapeutic benefit will, of course, be determined by the particular circumstances of the individual patient including, the size, weight, age and sex of the patient, the nature and stage of the disease, the aggressiveness of the disease, and the route of administration. For example, a daily dosage of from about 0.05 to about 50 mg/kg/day may be utilized. Higher or lower doses are also contemplated.

The practice of the invention is illustrated by the following non-limiting examples.

Procedure 1
General Procedure for Synthesis of Styryl and Benzyl Arylsulfones

To a solution of (8 g, 0.2 mol) sodium hydroxide in methanol (200 ml), appropriate thiophenol or benzyl mercaptan (0.1 mol) is added slowly. Then chloroacetic acid (0.1 mol) is added in portions and the reaction mixture is refluxed for 2–3 hours. The cooled contents are poured onto crushed ice and neutralized with dilute hydrochloric acid (200 ml). The resulting aryl and benzylthioacetic acids (0.1 mol) are subjected to oxidation with 30% hydrogen peroxide (0.12 mol) in glacial acetic acid (25 ml) by refluxing for 1–2 hours. The contents are cooled and poured onto crushed ice. The separated solid is recrystallized from hot water to give pure aryl and benzylsulfonyl acetic acids.

A mixture of the appropriate aryl or benzylsulfonyl acetic acid (0.001 mol), an aromatic aldehyde (0.001 mol) and benzylamine (1 ml) in glacial acetic acid (15 ml) is reflexed for 2–3 hours. The contents are cooled and treated with dry ether (50 ml). Any product separated is collected by filtration. The filtrate is diluted with more ether and washed successively with a saturated solution of sodium bicarbonate (20 ml), sodium bisulfite (20 ml), dilute hydrochloric acid (20 ml) and finally with water (35 ml). Evaporation of the dried ethereal layer yields a solid in many cases. However, in some cases a syrupy material separates and is solidified on treatment with 2-propanol. The purity of the compounds is checked by TLC (silica gel BDH, hexane/ethyl acetate 3:1).

Procedure 2
General Procedure for Synthesis of (E)(E)- and (E)(Z)-bis(Styryl)Sulfones To freshly distilled phenyl acetylene (51.07 g, 0.5 mol) is added sodium thioglycollate prepared from thioglycolic acid (46 g, 0.5 mol) and sodium hydroxide (40 g, 1 mol) in methanol (250 ml). The mixture is refluxed for 24 hours and poured onto crushed ice (500 ml) after cooling. The styrylthioacetic acid, formed after neutralization with dilute hydrochloric acid (250 ml), is filtered and dried; yield 88 g (90%); m.p. 84–86° C.

The styrylthioacetic acid is then oxidized to styrylsulfonylacetic acid as follows. A mixture of styrylthioacetic acid (5 g, 25 mmol) in glacial acetic acid (35 ml) and 30% hydrogen peroxide (15 ml) is heated under reflux for 60 minutes and the mixture is poured onto crushed ice (200 ml) after cooling. The compound separated is filtered and recrystallized from hot water to give white crystalline flakes of (Z)-styrylsulfonylacetic acid; yield 2.4 g (41%); m.p. 150–51° C.

A solution of (Z)-styrylsulfonylacetic acid (2.263 g, 10 m mol) in glacial acetic acid (6 ml) is mixed with an aromatic aldehyde (10 mmol) and benzylamine (0.2 ml) and refluxed for 3 hours. The reaction mixture is cooled, treated with dry ether (50 ml), and any product separated is collected by filtration. The filtrate is diluted with more ether and washed successively with a saturated solution of sodium hydrogen carbonate (15 ml), sodium bisulfite (15 ml), dilute hydrochloric acid (20 ml) and finally with water (30 ml). Evaporation of the dried ethereal layer yields (E)(Z)-bis(styryl)sulfones.

(E),(E)-bis(styryl)sulfones are prepared following the same procedure as described above with exception that sulfonyldiacetic acid is used in place of (Z)-styrylsulfonylacetic acid, and twice the amount of aromatic aldehyde (20 mmol) is used.

Procedure 3
General Procedure for the Synthesis of 2-(Arylsulfonyl)-1-phenyl-3-aryl-2-propen-1-ones These compounds are synthesized by two methods which employ different reaction conditions, solvents and catalysts.

Method 1: P7henacyl aryl sulfones are made by refluxing α-bromoacetophenones (0.05 mol) and sodium arylsulfinates (0.05 mol) in absolute ethanol (200 ml) for 6–8 hours. The product which separates on cooling is filtered and washed several times with water to remove sodium bromide. The product is then recrystallized from ethanol: phenacyl-phenyl sulfone, m.p. 90–91° C.; phenacyl-p-fluorophenyl sulfone, m.p. 148–149° C.; phenacyl-p-bromophenyl sulfone, m.p. 121–122° C.; phenacyl-p-methoxyphenyl sulfone, m.p. 104–105° C.; p-nitrophenacyl-phenyl sulfone, m.p. 136–137° C.

A solution of phenacyl aryl sulfone (0.01 mol) in acetic acid (10 ml) is mixed with an araldehyde (0.01 mol) and benzylamine (0.02 ml) and refluxed for 3 hours. The solution is cooled and dry ether (50 ml) is added. The ethereal solution is washed successively with dilute hydrochloric acid, aqueous 10% NaOH, saturated $NaHSO_3$ solution and water. Evaporation of the dried ethereal layer gives a solid product which is purified by recrystallization.

Method 2: Dry tetrahydrofuran (200 ml) is taken in a 500 ml conical flask flushed with nitrogen. To this, a solution of titanium (IV) chloride (11 ml, 0.01 mol) in absolute carbon tetrachloride is added dropwise with continuous stirring. The contents of the flask are maintained at −20° C. throughout the course of the addition. A mixture of phenacyl aryl sulfone (0.01 mol) and aromatic aldehyde (0.01 mol) is added to the reaction mixture and pyridine (4 ml, 0.04 mol) in tetrahydrofuran (8 ml) is added slowly over a period of 1 hour. The contents are stirred for 10–12 hours, treated with water (50 ml) and then ether (50 ml) is added. The ethereal layer is separated and washed with 15 ml of saturated solutions of 10% sodium hydroxide, sodium bisulfite and brine. The evaporation of the dried ethereal layer yields 2-(arylsulfonyl)-1-phenyl-3-aryl-2 propen-1-ones.

EXAMPLE 1

E-styryl Phenyl Sulfone

A solution of phenyl sulfonylacetic acid (0.01 mol) and benzaldehyde (0.01 mol) was subjected to the Procedure 1. The title compound was obtained in 68–72% yield.

EXAMPLE 2

E-4-chlorostyryl Phenyl Sulfone

A solution of phenyl sulfonylacetic acid (0.01 mol) and 4-chlorobenzaldehyde (0.01 mol) was subjected to Procedure 1. The title compound was obtained in 78–80% yield.

EXAMPLE 3

E-2,4-dichlorostyryl Phenyl Sulfone

A solution of phenyl sulfonylacetic acid (0.01 mol) and 2,4-dichlorobenzaldehyde (0.01 mol) was subjected to Procedure 1. The title compound was obtained in 60–65% yield.

EXAMPLE 4

E-4-bromostyryl Phenyl Sulfone

A solution of phenyl sulfonylacetic acid (0.01 mol) and 4-bromobenzaldehyde (0.01 mol) was subjected to Procedure 1. The title compound was obtained in 78–80% yield.

EXAMPLE 5

E-4-chlorostyryl 4-chlorophenyl Sulfone

A solution of 4-chlorophenyl sulfonylacetic acid (0.01 mol) and 4-chlorobenzaldehyde (0.01 mol) was subjected to Procedure 1. The title compound was obtained in 70–72% yield.

EXAMPLE 6

E-4-methylstyryl 4-chlorophenyl Sulfone

A solution of 4-chlorophenyl sulfonylacetic acid (0.01 mol) and 4-methylbenzaldehyde (0.01 mol) was subjected to Procedure 1. The title compound was obtained in 60–64% yield.

EXAMPLE 7

E-4-methoxystyryl 4-chlorophenyl Sulfone

A solution of 4-chlorophenyl sulfonylacetic acid (0.01 mol) and 4-methoxybenzaldehyde (0.01 mol) was subjected to Procedure 1. The title compound was obtained in 68–70% yield.

EXAMPLE 8

E-4-bromostyryl 4-chlorophenyl Sulfone

A solution of 4-chlorophenyl sulfonylacetic acid (0.01 mol) and 4-bromobenzaldehyde (0.01 mol) was subjected to Procedure 1. The title compound was obtained in 80% yield.

EXAMPLE 9

E-2-chlorostyryl Benzyl Sulfone

A solution of benzyl sulfonylacetic acid (0.01 mol) and 2-chlorobenzaldehyde (0.01 mol) was subjected to Procedure 1. The title compound was obtained in 72% yield.

EXAMPLE 10

E-4-chlorostyryl Benzyl Sulfone

A solution of benzyl sulfonylacetic acid (0.01 mol) and 4-chlorobenzaldehyde (0.01 mol) was subjected to Procedure 1. The title compound was obtained in 78% yield.

EXAMPLE 11

E-4-fluorostyryl 4-chlorobenzyl Sulfone

A solution of 4-chlorobenzyl sulfonylacetic acid (0.01 mol) and 4-fluorobenzaldehyde (0.01 mol) was subjected to Procedure 1. The title compound was obtained in 72% yield.

EXAMPLE 12

E-4-chlorostyryl 4-chlorobenzyl Sulfone

A solution of 4-chlorobenzyl sulfonylacetic acid (0.01 mol) and 4-chlorobenzaldehyde (0.01 mol) was subjected to Procedure 1. The title compound was obtained in 80% yield.

EXAMPLE 13

E-4-fluorostyryl 4-fluorobenzyl Sulfone

A solution of 4-fluorobenzyl sulfonylacetic acid (0.01 mol) and 4-fluorobenzaldehyde (0.01 mol) was subjected to Procedure 1. The title compound was obtained in 73% yield.

EXAMPLE 14

E-2,4-difluorostyryl 4-fluorobenzyl Sulfone

A solution of 4-fluorobenzyl sulfonylacetic acid (0.01 mol) and 2,4difluorobenzaldehyde (0.01 mol) was subjected to Procedure 1. The title compound was obtained in 68% yield.

EXAMPLE 15

E-4-fluorostyryl 4-bromobenzyl Sulfone

A solution of 4-bromobenzyl sulfonylacetic acid (0.01 mol) and 4-fluorobenzaldehyde (0.01 mol) was subjected to Procedure 1. The title compound was obtained in 82% yield.

EXAMPLE 16

E-4-bromostyryl 4-bromobenzyl Sulfone

A solution of 4-bromobenzyl sulfonylacetic acid (0.01 mol) and 4-bromobenzaldehyde (0.01 mol) was subjected to Procedure 1. The title compound was obtained in 88% yield.

EXAMPLE 17

E-4-bromostyryl 4-fluorobenzyl Sulfone

A solution of 4-fluorobenzyl sulfonylacetic acid (0.01 mol) and 4-bromobenzaldehyde (0.01 mol) was subjected to Procedure 1. The title compound was obtained in 82% yield.

EXAMPLE 18

E-4-chlorostyryl 4-bromobenzyl Sulfone

A solution of 4-bromobenzylsulfonyl acetic acid (0.01 mol) and 4-chlorobenzaldehyde (0.01 mol) was subjected to Procedure 1. The title compound was obtained in 88% yield.

EXAMPLE 19

E-4-bromostyryl 4-chlorobenzyl Sulfone

A solution of 4-chlorobenzylsulfonyl acetic acid (0.01 mol) and 4-bromobenzaldehyde (0.01 mol) was subjected to Procedure 1. The title compound was obtained in 92% yield.

EXAMPLE 20

(Z)-styryl-(E)-4-fluorostyryl Sulfone

A solution of (Z)-styryl sulfonylacetic acid (0.01 mol) and 4—4-fluorobenzaldehyde (0.01 mol was subjected to Procedure 2. The title compound was obtained in 68% yield.

EXAMPLE 21

(Z)-styryl-(E)-4-bromostyryl Sulfone

A solution of (Z)-styryl sulfonylacetic acid (0.01 mol) and 4-bromobenzaldehyde (0.01 mol) was subjected to Procedure 2. The title compound was obtained in 70% yield.

EXAMPLE 22

(Z)-styryl-(E)-4-chlorostyryl Sulfone

A solution of (Z)-styryl sulfonylacetic acid (0.01 mol) and 4-chlorobenzaldehyde (0.01 mol) was subjected to Procedure 2. The title compound was obtained in 64% yield.

EXAMPLE 23

2-[(4-fluorophenyl)sulfonyl]-1-phenyl-3-(4-fluorophenyl)-2-propen-1-one

A solution of phenacyl-4-fluorophenyl sulfone (0.01 mol) and 4-fluorobenzaldehyde (0.01 mol) was subjected to Method 1 of Procedure 3. The title compound was obtained in 63% yield.

EXAMPLE 24

2-[(2-chlorophenyl-sulfonyl]-1-phenyl-3-(4-fluorophenyl)-2-propen-1-one

A solution of phenacyl-2-chlorophenyl sulfone (0.01 mol) and 4-fluoro benzaldehyde (0.01 mol) was subjected to Method 1 of Procedure 3. The title compound was obtained in 58% yield.

EXAMPLE 25

2-[(2-chlorophenyl)sulfonyl]-1-phenyl-3-(4-bromophenyl)-2-propen-1-one

A solution of phenacyl-2-chlorophenyl sulfone (0.01 mol) and 4-bromo benzaldehyde (0.01 mol) was subjected to Method 1 of Procedure 3. The title compound was obtained in 66% yield.

EXAMPLE 26

2-[(4-chlorophenyl)sulfonyl]-1-phenyl-3-(4-bromophenyl)-2-propen-1-one

A solution of phenacyl-4-chlorophenyl sulfone (0.01 mol) and 4-bromo benzaldehyde (0.01 mol) was subjected to Method 1 of Procedure 3. The title compound was obtained in 60% yield.

EXAMPLE 27

2-[(2-nitrophenyl)sulfonyl]-1-phenyl-3-(4-bromophenyl)-2-propen-1-one

A solution of phenacyl-2-nitrophenyl sulfone (0.01 mol) and 4-bromo benzaldehyde (0.01 mol) was subjected to Method 1 of Procedure 3. The title compound was obtained in 56% yield.

Infrared and nuclear magnetic resonance spectroscopy analysis of the example compounds provided the data set forth in Table 1:

TABLE 1

IR and NMR Spectroscopy

| Ex | IR (KR pellet) vC=C | vSO$_2$ | NMR (CDCl$_3$) (δ ppm) |
|---|---|---|---|
| 1 | 1638 | 1380,1140 | 6.81(1H, d, J$_{H,H}$ = 15.6), 7.2–7.8(m, 10H), 7.49(1H, d) |
| 2 | 1627 | 1368,1155 | 6.88(1H, d, J$_{H,H}$ = 15.2), 7.15–7.9(m, 9h), 7.54(1H, d) |
| 3 | 1635 | 1370,1140 | 6.92(1H, d, J$_{H,H}$ = 15.6), 7.3–7.85(m, 9H), 7.62(1H, d) |
| 4 | 1642 | 1355,1142 | 6.90(1H, d, J$_{H,H}$ = 15.4), 7.25–7.9(m, 9H), 7.58(1H, d) |
| 5 | 1645 | 1328,1126 | 6.86(1H, d, J$_{H,H}$ = 15.6), 7.30–7.75(m, 8H), 7.55(1H, d) |
| 6 | 1650 | 1344,1116 | 2.45(3H, s), 6.83(1H, d, J$_{H,H}$ = 15.8), 7.25–7.85(m, 8H), 7.48(1H, d) |
| 7 | 1658 | 1320,1128 | 3.85(3H, s), 6.85(1H, d, J$_{H,H}$ = 15.4), 7.28–7.82(m, 8H), 7.60(1H, d) |
| 8 | 1660 | 1311,1148 | 6.84(1H, d, J$_{H,H}$ = 15.6), 7.25–7.8(m, 8H), 7.60(1H, d) |
| 9 | 1638 | 1318,1140 | 4.30(2H, s), 6.81(1H, d, J$_{H,H}$ = 15.6), 7.30–7.75(m, 9H), 7.58(1H) |
| 10 | 1642 | 1312,1140 | 4.34(2H, s), 6.78(1H, d, J$_{H,H}$ = 15.7), 7.26–7.85(m, 9H), 7.54(1H) |
| 11 | 1650 | 1305,1150 | 4.32(2H, s), 6.82(1H, d, J$_{H,H}$ = 16.0), 7.22–7.76(m, 8H), 7.52(1H) |
| 12 | 1658 | 1316,1132 | 4.38(2H, s)6.86(1H, d, J$_{H,H}$ = 16.2), 7.26–7.85(m, 8H), 7.58(1H) |
| 13 | 1640 | 1307,1132 | 4.44(2H, s),6.84(1H, d, J$_{H,H}$ = 15.8), 7.20–7.78(m, 8H), 7.58(1H) |
| 14 | 1646 | 1326,1145 | 4.40(2H, s), 6.88(1H, d, J$_{H,H}$ = 15.6), 7.33–7.72(m, 7H), 7.58(1H) |
| 15 | 1660 | 1330,1144 | 4.46(2H, s), 6.90(1H, d, J$_{H,H}$ = 16.2), 7.24–7.78(m, 8H), 7.58(1H) |
| 16 | 1658 | 1316,1132 | 4.38(2H, s), 6.76(1H, d, J$_{H,H}$ = 16.3), 7.36–7.84(m, 8H), 7.58(1H) |
| 17 | 1644 | 1314,1152 | 4.43(2H, s), 6.84(1H, d, J$_{H,H}$ = 15.8), 7.28–7.76(m, 8H), 7.60(1H) |
| 18 | 1652 | 1321,1148 | 4.42(2H, s), 6.78(1H, d, J$_{H,H}$ = 16.0), 7.34–7.80(m, 8H), 7.54(1H) |
| 19 | 1638 | 1330,1138 | 4.38(2H, s), 6.82(1H, d, J$_{H,H}$ = 15.6), 7.28–7.78(m, 8H), 7.55(1H) |
| 20 | — | 1300,1120 | 6.55(1H, d, J$_{H,H}$ = 10.8), 6.70(1H, d, J$_{H,H}$ = 14.8), 7.20–7.92(m, 9H aromatic, 2H vinyl) |
| 21 | — | 1318,1128 | 6.68(1H, d, J$_{H,H}$ = 11.0), 6.86(1H, d, J$_{H,H}$ = 15.0), 7.15–7.90(m, 9H aromatic, 2H vinyl) |
| 22 | — | 1330,1100 | 6.65(1H, d, J$_{H,H}$ = 11.2), 6.81 (1H, d, J$_{H,H}$ = 15.4), 7.00–7.85(m, 9H aromatic, 2H vinyl) |
| 23 | 1620 | 1320,1145 | 8.04(1H, s, —C=CH) 7.35–7.95(m, 13H) |
| 24 | 1625 | 1320,1148 | 8.48(1H, s, —C=CH) 7.40–8.25(m, 13H) |
| 25 | 1618 | 1315,1140 | 8.05(1H, s, —C=CH) 7.28–8.00(m, 13H) |
| 26 | 1620 | 1318,1142 | 8.47(1H, s, —C=CH) 7.30–8.15(m, 13H) |
| 27 | 1618 | 1315,1140 | 8.57(1H, s, —C=CH) 7.40–8.20(m, 13H) |

EXAMPLE 28

Tumor Cell Growth Inhibition by Styryl Sulfones

A. Cells

The effect of the styryl sulfones on the growth of normal and tumor cells of breast and prostate was examine utilizing four cell lines, NIH3T3, MCF-7, BT-20 and LnCap. NIH/3T3 cells represent normal fibroblasts while LnCap is an androgen-dependent prostate tumor cell line. MCF-7 is an estrogen-responsive breast tumor cell line, while BT-20 is an estrogen-unresponsive breast tumor cell line. MCF-7 and BT-20 were grown in Dulbecco's modified Eagle's medium (DMEM) containing 10% fetal bovine serum supplemented with penicillin and streptomycin. LnCaP were cultured in RPMI with 10% fetal bovine serum containing penicillin and streptomycin. NIH3T3 cells were grown in DMEM containing 10% calf serum supplemented with penicillin and streptomycin. All cell cultures were maintained at 37° C. in a humidified atmosphere of 5% $CO_2$.

B. Treatment with Styryl Sulfones and Viability Assay

Cells were treated with test compound at 2.5 μM or 5.0 μM concentration and cell viability was determined after 48 hours by the Trypan blue exclusion method. The compounds identified in Tables 2, 3 and 4 inhibited cell growth and induced cell death, to varying degrees. The tables list the percent viable LnCap and MCF-7 cells treated with 5.0 μM compound.

TABLE 2

II

| Example | n | $R_1$ | $R_2$ | $R_3$ | % viable LnCaP and MCF-7 cells |
|---|---|---|---|---|---|
| 1 | 0 | H | H | H | 89 |
| 2 | 0 | H | Cl | H | 90 |
| 3 | 0 | H | Cl | Cl | 88 |
| 4 | 0 | H | Br | H | 68 |
| 5 | 0 | Cl | Cl | H | 64 |
| 6 | 0 | Cl | $CH_3$ | H | 92 |
| 7 | 0 | Cl | $OCH_3$ | H | 90 |
| 8 | 0 | Cl | Br | H | 69 |
| 9 | 1 | H | H | Cl | 94 |
| 10 | 1 | H | Cl | H | 87 |
| 11 | 1 | Cl | F | H | 6 |
| 12 | 1 | Cl | Cl | H | 49 |
| 13 | 1 | F | F | H | 43 |
| 14 | 1 | F | F | F | 56 |
| 15 | 1 | Br | F | H | 7 |
| 16 | 1 | Br | Br | H | 51 |
| 17 | 1 | F | Br | H | 42 |
| 18 | 1 | Br | Cl | H | 7 |
| 19 | 1 | Cl | Br | H | 20 |

TABLE 3

III

| Example | $R_1$ | % viable LnCaP and MCF-7 cells |
|---|---|---|
| 20 | F | 76 |
| 21 | Br | 68 |
| 22 | Cl | 72 |

TABLE 4

IV

| Example | $R_1$ | $R_2$ | % viable LnCaP and MCF-7 cells |
|---|---|---|---|
| 23 | F | 4-fluorophenyl | 76 |
| 24 | F | 2-chlorophenyl | 64 |
| 25 | Br | 2-chlorophenyl | 72 |
| 26 | Br | 4-chlorophenyl | 58 |
| 27 | Br | 2-nitrophenyl | 74 |

Figure 1B:
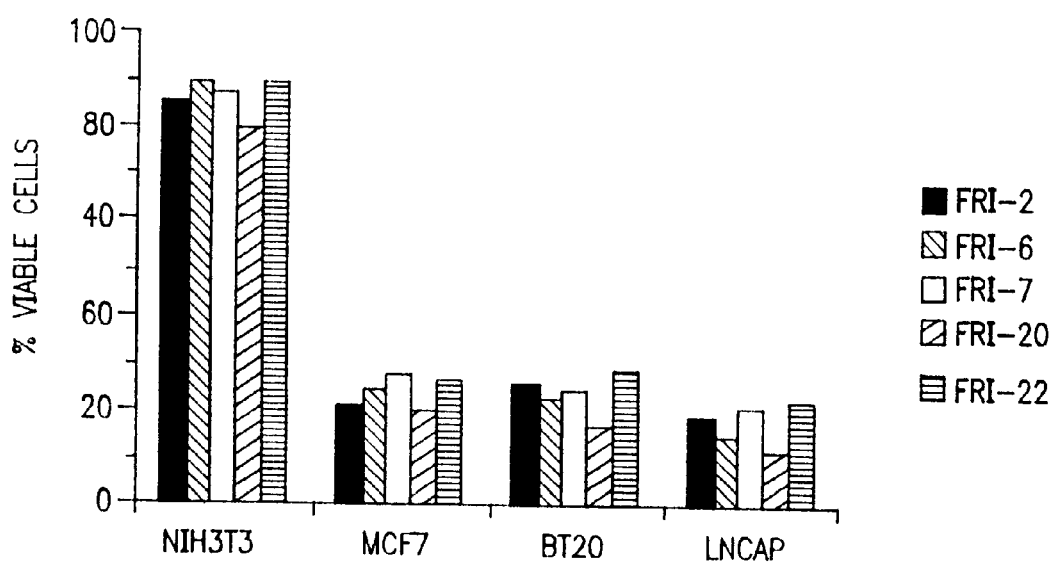

Five of the more active compounds which exhibited the highest activity were designated as FRI-2 (E-2,4-difluorostyrl-4-fluorobenzyl sulfone), FRI-6 (E-4-fluorostyryl 4-bromobenzyl sulfone), FRI-7 (E-4-bromostyryl 4-fluorobenzyl sulfone), FRI-20 (E-4-fluorostyryl 4-chlorobenzyl sulfone) and FRI-22 (E-4-chlorostyryl 4-chlorobenzyl sulfone). These compounds were found to substantially inhibit the growth and induce the death of LnCaP, BT-20 and MCF-7 cells at 2.5 mM (FIG. 1A) and 5.0 mM (FIG. 1B), after 48 hours of treatment with the compounds. Under identical conditions, more than 80% of NIH3T3 cells were viable after 48 hours incubation (FIG. 1A and 1B). E-4-chlorostyryl 4-bromobenzyl sulfone and E-4-bromostyryl 4-chlorobenzyl sulfone were also highly active.

C. Dose-Dependency Assay

Figure 2A:
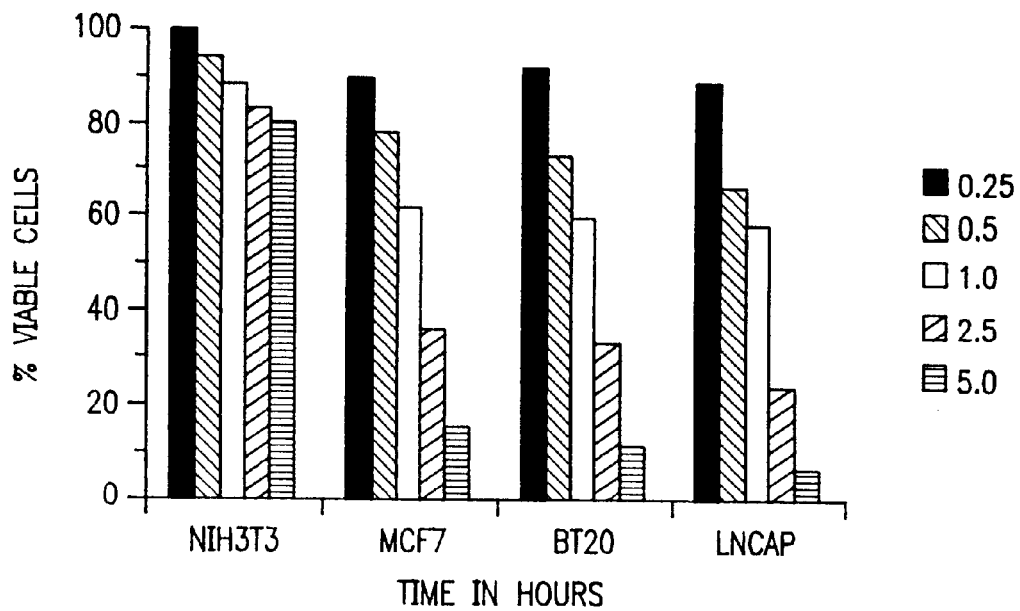
FIG. 2A is a bar graph of the concentration dependent inhibition of MCF7, BT20, LnCaP and NIH3T3 cells by treatment with FRI-20. The cells were treated with 0, 250 nM, 500 nM, 1 $\mu$M, 2.5 $\mu$M and 5.0 $\mu$M FRI-20 for 48 hours. The percentage of living cells was determined by Trypan blue exclusion. The mean of three independent experiments is shown.

The dose dependency of the styryl sulfone was established by treating the cells with FRI-20, one of the five most active compounds. NIH3T3, MCF-7, BT-20 and LnCaP cells were treated with FRI-20 dissolved in DMSO to concentrations of 250 nM, 500 nM, 1 μM, 2.5 μM and 5 μM and examined for their proliferation and viability after 48 hours (FIG. 2A). The percentage of living cells was determined by Trypan blue exclusion. The control cells were treated with DMSO to determine the effect of solvent on cells. At a concentration of 250 nM, there was about 10% cell death in MCF-7, BT-20 and LnCaP cells and about 15–20% inhibition in cell division compared to untreated cells after 48 hours. There was about 30–50% inhibition in cell proliferation and 25–30% cell death in LnCap, BT-20 and MCF-7 at 500 nM concentration. Under these conditions, only 2–3% of NIH3T3 cells were non-viable at both the concentrations. The LnCaP, BT-20 and MCF-7 cell growth was greatly inhibited by 1 μM concentration of FRI-20 with concomitant loss of cell viability. After 48 hours incubation, 60–75% of the LnCaP, BT-20 and MCF-7 cells were dead at 2.5 mM FRI-20 concentration, whereas more than 90% of NIH3T3 cells were viable (FIG. 2A). The LnCap, BT-20 and MCF-7 cells treated with 5 μM FRI-20 (FIG. 2A) showed nearly 90% cell death. NIH3T3 showed little or no alteration in their ability to grow and maintain >80% viability in the presence of FRI-2, -6, -7, -20 or -22, at 5 μM concentration.

D. Time Course Assay

Figure 2B:
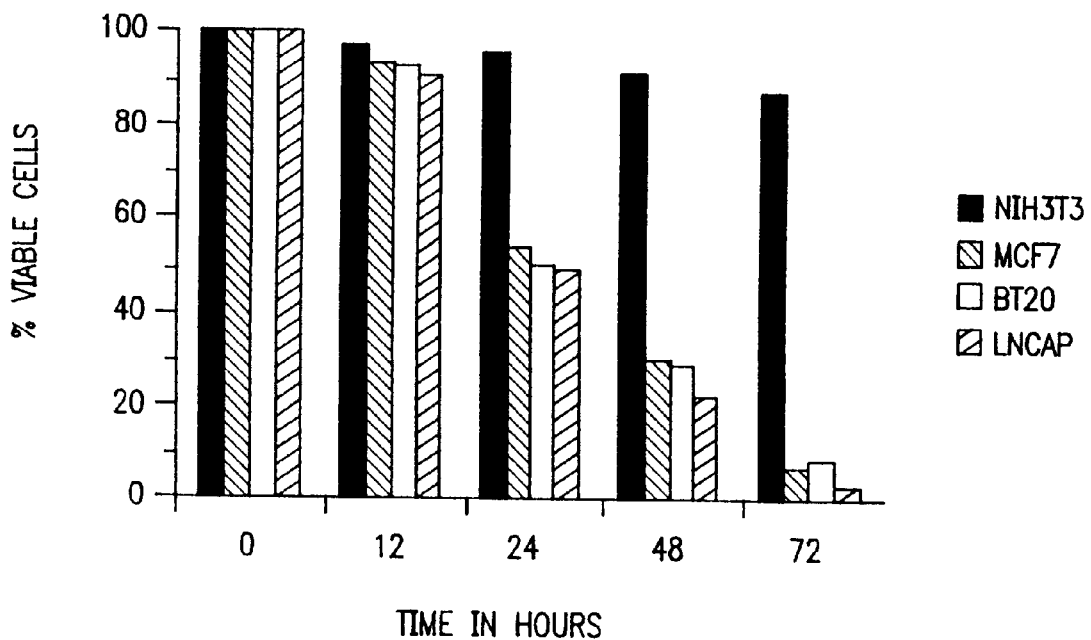
FIG. 2B is a bar graph of the viability of MCF7, BT20, LnCaP and NIH3T3 cells after treatment with FRI-20 at different time periods. All the cells were treated with FRI-20 at 2.5 $\mu$M, and the number of viable cells was determined at 12, 24, 48, and 72 hours by Trypan blue exclusion. The mean of three independent experiments is shown.

The time course of the activity of FRI-20 was demonstrated as follows. NIH/3T3, MCF-7, BT-20 and LnCap were treated with FRI-20 at 2.5 μM and the number of viable cells was determined at 12, 24, 48 and 72 hours by Trypan blue exclusion. The mean of three independent experiments is shown in FIG. 2B. The time course study revealed that more than 95% of MCF-7, LnCaP and BT-20 cells were dead after 72 hours of treatment with FRI-20 at 2.5 μM (FIG. 2B).

EXAMPLE 29

Tumor Cell Growth Inhibition by FRI-20

A. Cells

The effect of FR-20 on the growth of normal and tumor cells of breast and prostate was examine utilizing nine cell lines: NIH/3T3 and HFL (normal fibroblast cell lines); MCF-7 and 361 (estrogen-receptor negative breast tumor cell lines); BT-20, 435 and SKBR-3 (estrogen-receptor positive breast tumor cell lines); LnCaP (androgen sensitive prostate tumor cell line); PC-3 and DU-145 (androgen insensitive prostate tumor cell line).

B. Treatment with FRI-20 and Viability Assay

Figure 3A:
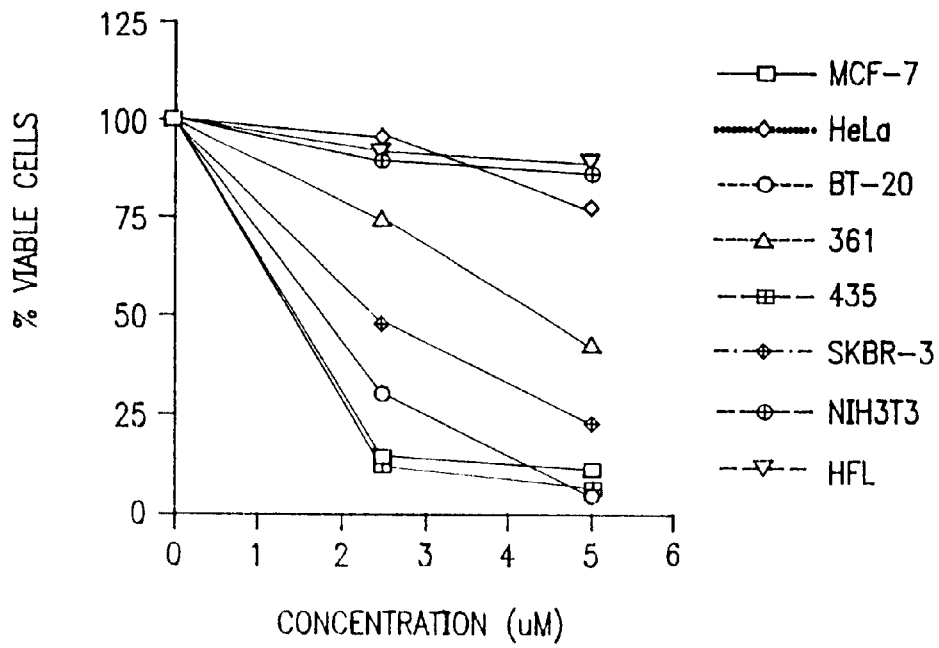
FIG. 3A is a plot of the activity of compound FRI-20 on the normal cell lines NIH3T3, HeLa and HFL; the estrogen receptor-positive breast tumor cell lines MCF-7 and 361; the estrogen receptor-negative breast tumor cell lines SKBR-3, 435 and BT-20).
Figure 3B:
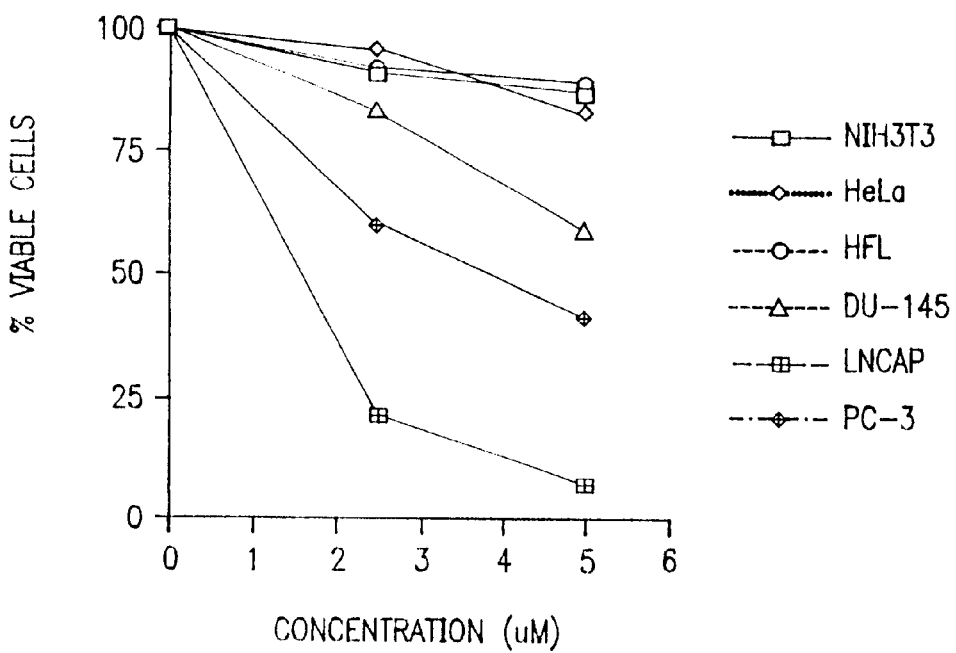
FIG. 3B is similar to FIG. 3A except the treated cells comprise the androgen-dependent prostate cell line LnCaP, and the androgen independent prostate cell lines DU-145 and PC-3). All cells were treated with 2.5 and 5.0 $\mu$M concentration of FRI-20 and assayed for cell viability after 48 hours by Trypan blue exclusion. The mean of three experiments is shown. Variance did not exceed 10%.
Figure 4A:
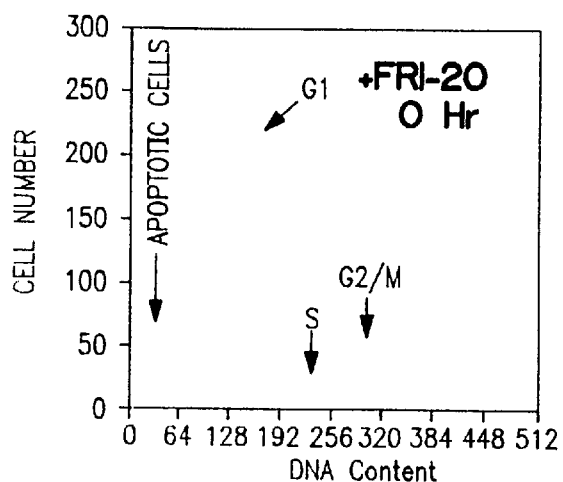
FIGS. 4A–4H comprise a series of blots of the cell cycle analysis of FRI-20-treated or control-treated LnCaP cells. LnCaP cells were treated with 120 ml of DMSO (control cells) or 2.5 μM FRI-20 in 10 ml of DMSO. Cells were harvested 6, 12, 24 and 48 hours following treatment and stained with propidium iodide and subjected to flow cytometry.
Figure 4B:
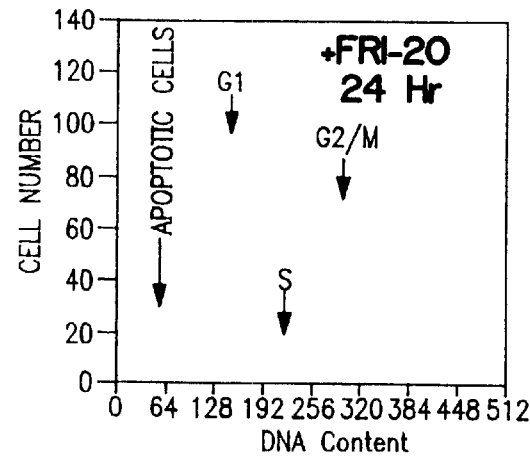
Figure 4C:
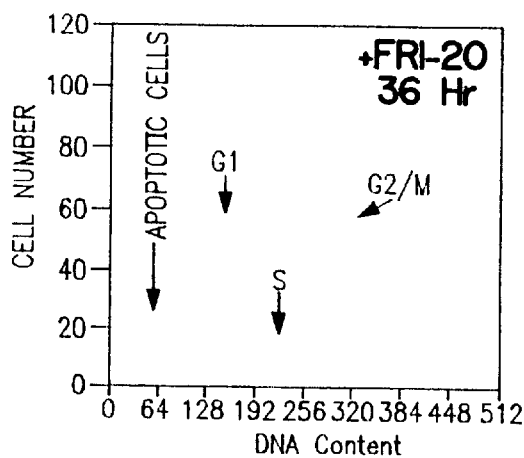
Figure 4D:
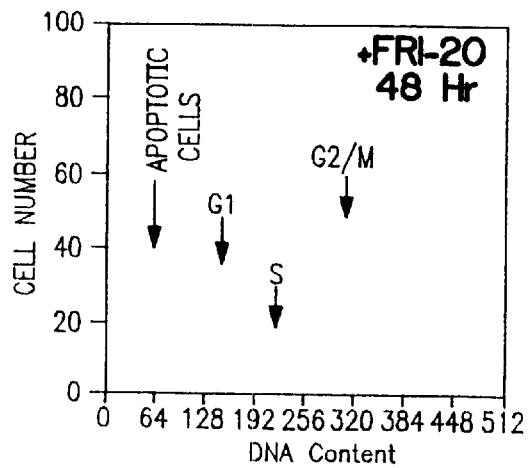
Figure 4E:
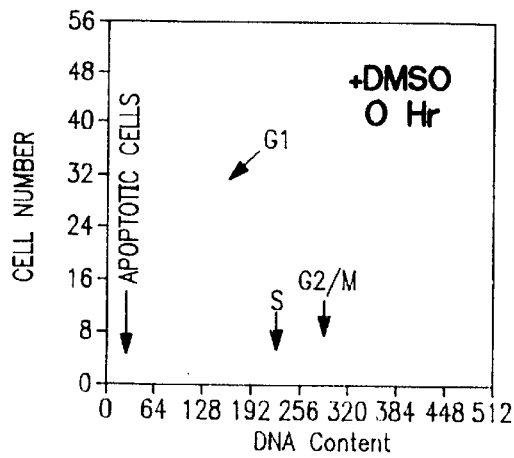
Figure 4F:
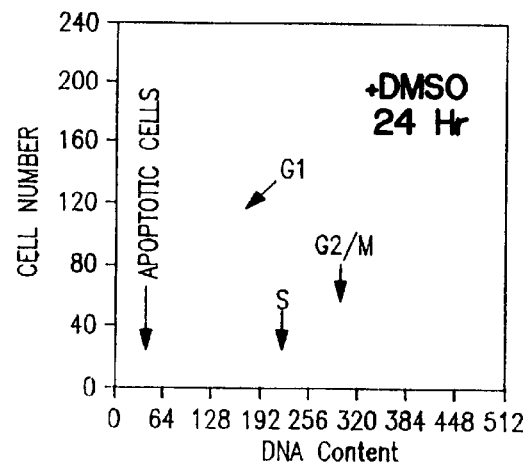
Figure 4G:
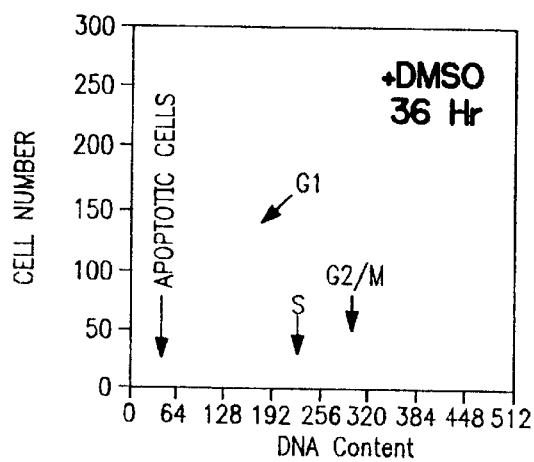
Figure 4H:
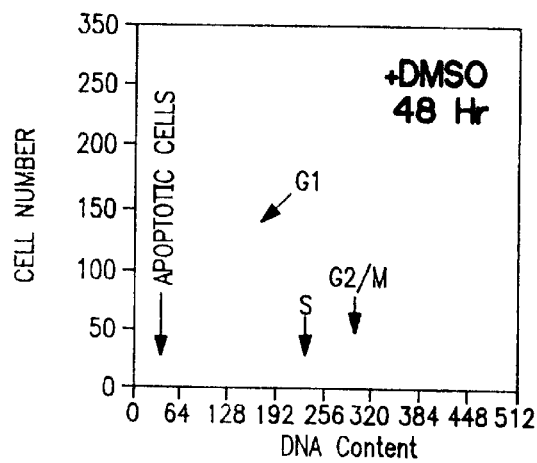

The cells were grown as in Example 22, A. FR-20 was dissolved in DMSO and added to the cells at 2.5 μM and 5.0 μM concentration. To control cells, DMSO was added equivalent to the volume of solvent (DMSO) present at the highest concentration of the compound. The activity of the compound was evaluated after 48 hours by Trypan blue exclusion. NIH3T3 and HFL cells were found to maintain a percent viability of 85–90% at 2.5 and 5.0 μM concentration. Of the seven breast tumor cell lines treated with FRI-20 compound, MCF-7, HTB126, T470 and 435 cells showed very high mortality with less than 25% and 10% viability at 2.5 and 5.0 μM concentrations of the drug (FIG. 3A). Nearly 50% of SKBR-3 and BT-20 cells were dead at 2.5 μM and 75% at 5.0 μM concentration of the compound. The 361 breast tumor cell line, on the other hand showed considerable resistance to FRI-20 with 50–75% of cells being viable at 2.5 and 5.0 μM concentration. FRI-20 had profound effect on the viability of androgen-dependent LnCaP prostate tumor cell line when compared to androgen-independent DU-145 and PC-3 prostate cell lines. At 2.5 mM FRI-20, 80% of LnCaP, 40% of PC-3 and 20% of DU-145 cells were killed. At 5.0 mM FRI-20, 72% of LnCaP, 47% of PC-3 and 40% of DU-145 were killed (FIG. 3B).

EXAMPLE 30

Effect of FRI-20 on Cell Cycle Regulation

The androgen-dependent prostate tumor cell line LnCaP was grown as in Ex. 22, A, and treated with 2.0 μM FRI-20 dissolved in DMSO or with equivalent amounts (10 ml) of DMSO alone. Cells were harvested 6, 12, 24, and 48 hours following treatment and stained with propidium iodide and subjected to flow cytometry (FACS) for analysis of DNA content. As shown in FIG. 4, the addition of FR-20 to the culture medium results in the accumulation of cells in the G2/M phase of the cell cycle and as the cells exit this phase of the cell cycle, they appeared to undergo apoptosis (FIGS. 4A–4D). Cells treated with DMSO alone failed to exhibit such an arrest in the G2/M phase of the cell cycle, suggesting that the effects seen are associated with FRI-20 addition (FIGS. 4E–4H). Treatment of the normal cell lines NIH3T3 or HFL with FRI-20 failed to produce a similar effect on cell cycle progression. NIH3T3 and HFL exhibited normal cell cycle progression in the presence and absence of drug.

EXAMPLE 31

Effect of FRI-20 on MPK Pathway

A. Immune Complex ERK-2 Assay

To examine the effects of FRI-20 on the MAPK pathway, NIH3T3, LnCaP and MCF-7 cells were incubated with FRI-20 at a concentration 2.5 mM for 48 hours. Following incubation of cells in the presence and absence of FRI-20, the cells were lysed using ERK lysis buffer containing 20 mM HEPES (pH 7.4), 50 mM β-glycerophosphate, 0.5% Triton X-100, 2 mM $MgCl_2$, 1 mM EGTA, 1 mM dithiothreitol, 2 μg/ml leupeptin, 2 μg/ml aprotinin, 100 μM phenylmethylsulfonyl fluoride, and 1 mM benzamidine. ERK-2 in 100 mg of cell lysate was immunoprecipitated by incubating lysate protein with 1 mg of ERK-2 polyclonal antibody (antibody sc-154 to ERK2 is from Santa Cruz Biotechnology, Inc.) for one hour followed by an additional incubation of 20 μl of protein A-Sepharose (Pharmacia) for one hour. The immune complex-bound protein A-Sepharose beads were washed twice with lysis buffer and twice with ERK/MAPK buffer containing 20 mM HEPES (pH 7.4), 50 mM β-glycerophosphate, 10 mM $MgCl_2$, 1 mM EGTA, 1 mM dithiothreitol, and 100 MM $Na_3VO_4$.

Figures 5, 7:
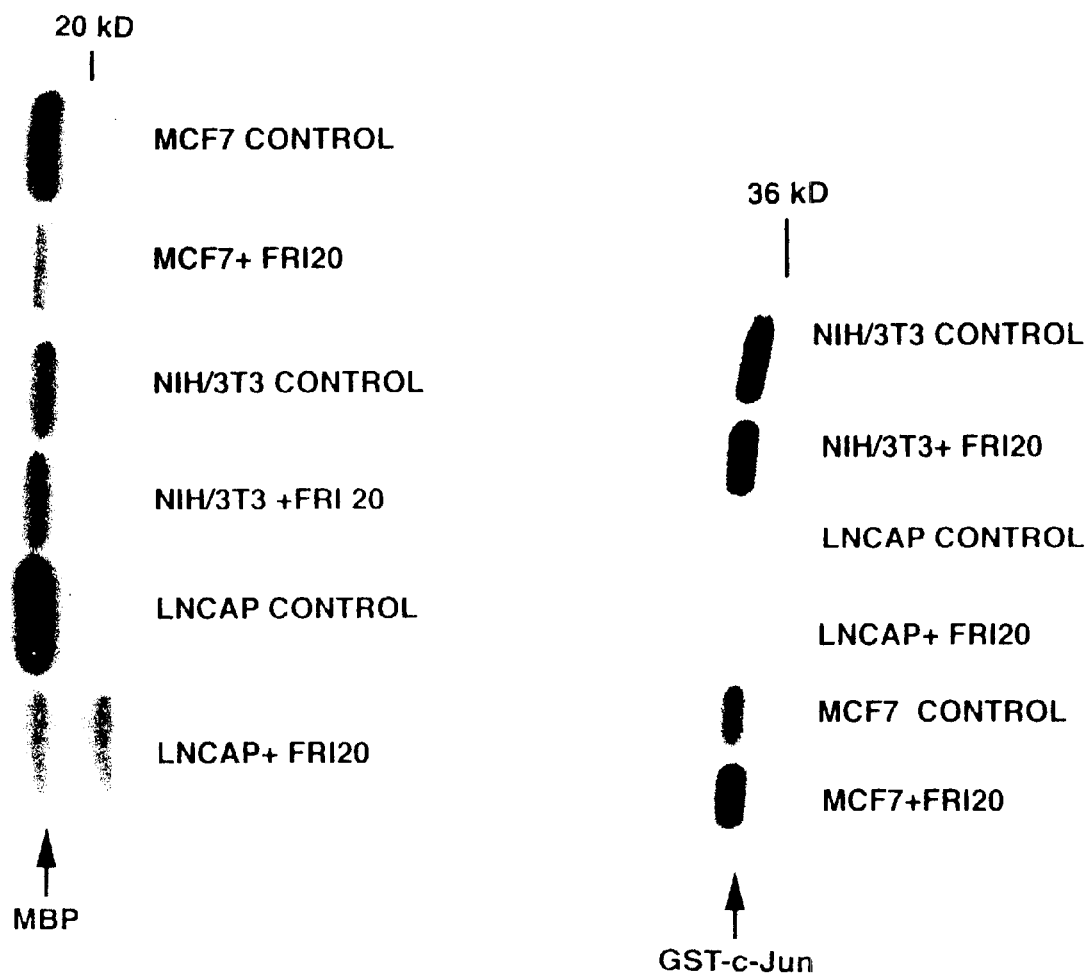
FIG. 5 is an SDS-PAGE autoradiograph of the effect of FRI-20 on ERK/MAPK activity. FRI-20-treated LnCaP, MCF-7 and NIH3T3 cells, along with DMSO-treated cells (control), were processed for ERK/MAPK immune complex kinase essay using myelin basic protein (MBP) as a substrate. The activity of ERK-2 toward MBP was then assayed in the presence of [$\gamma^{32}$P]ATP. The phosphorylated MBP was separated on 12% SDS-PAGE and visualized by autoradiography.
FIG. 7 is an SDS-PAGE autoradiograph of the effect of FRI-20 on JNK/SAPK activity. JNK was immunoprecipitated from 100 mg of cultured cell lysates with JNK polyclonal antibody, and an immune complex kinase assay was carried out using GST-c-Jun (1–79) as a substrate. The phosphorylated proteins were separated by SDS-PAGE and visualized by autoradiography. The experiment was repeated three times with similar results.

The immunoprecipitates were then tested for MAP kinase activity by an in vitro assay which utilizes myelin basic proteins (MBP) as a substrate for ERK-2 in the presence of [$\gamma$-$^{32}$P] ATP. Accordingly, the beads were resuspended in 40 μl of MAPK buffer containing 100 μM [$\gamma$-$^{32}$P] ATP (5000 cpm/pmol), and the kinase assay was carried out for 20 minutes at 30° C. using 5 μg of MBP as substrate. The reaction was stopped by the addition of Laemmli's buffer followed by the boiling of the samples for 3 minutes. The proteins were resolved on 12% SDS-PAGE; the gel was dried, and an autoradiogram was developed. The results show that both drug-treated and untreated cells exhibit similar levels of intracellular ERK-2, but the biochemical activity of ERK-2, as judged by its ability to phosphorylate MBP, was considerably diminished in drug-treated cells compared to cells treated with DMSO alone. In prostate tumor cells, FRI-20 reduced the phosphorylation status of MBP by more than 80% compared to mock-treated cells (FIG. 5).

B. Western Blot Analysis

Cell lysates of FRI-20-treated cells were prepared for Western Blot analysis as follows. NIH3T3, LnCaP or MCF-7 cells were seeded at a density of $2 \times 10^5$ cells/per well in a six-well plate and allowed to grow for 24 hours. Fresh medium was added to each well 2 hours before treatment with FRI-20. The compound was dissolved in DMSO to make a 2 mM stock solution and added to the medium (2 ml) to obtain a final concentration of 2.5 and 5.0 μM. After 48 hours at 37° C., the cells were washed twice with 10 ml of ice cold phosphate-buffered saline and harvested in 400 μl of lysis buffer containing 25 mM HEPES (pH 7.6), 0.1% Triton X-100, 300 mM NaCl, 1.5 mM $MgCl_2$, 20 mM β-glycerophosphate, 100 μM $Na_3VO_4$, 0.2 mM EDTA, 0.5 mM dithiothreitol, 2 μg/ml aprotinin, 2 μg/ml leupeptin, 100 μM phenylmethylsulfonyl chloride and 1 mM benzamidine. The cell lysates were kept on ice for 30 minutes and centrifuged for 10 minutes in a microcentrifuge (16000 X g). The cell lysates were separated from the debris and normalized for protein content.

Figure 6:
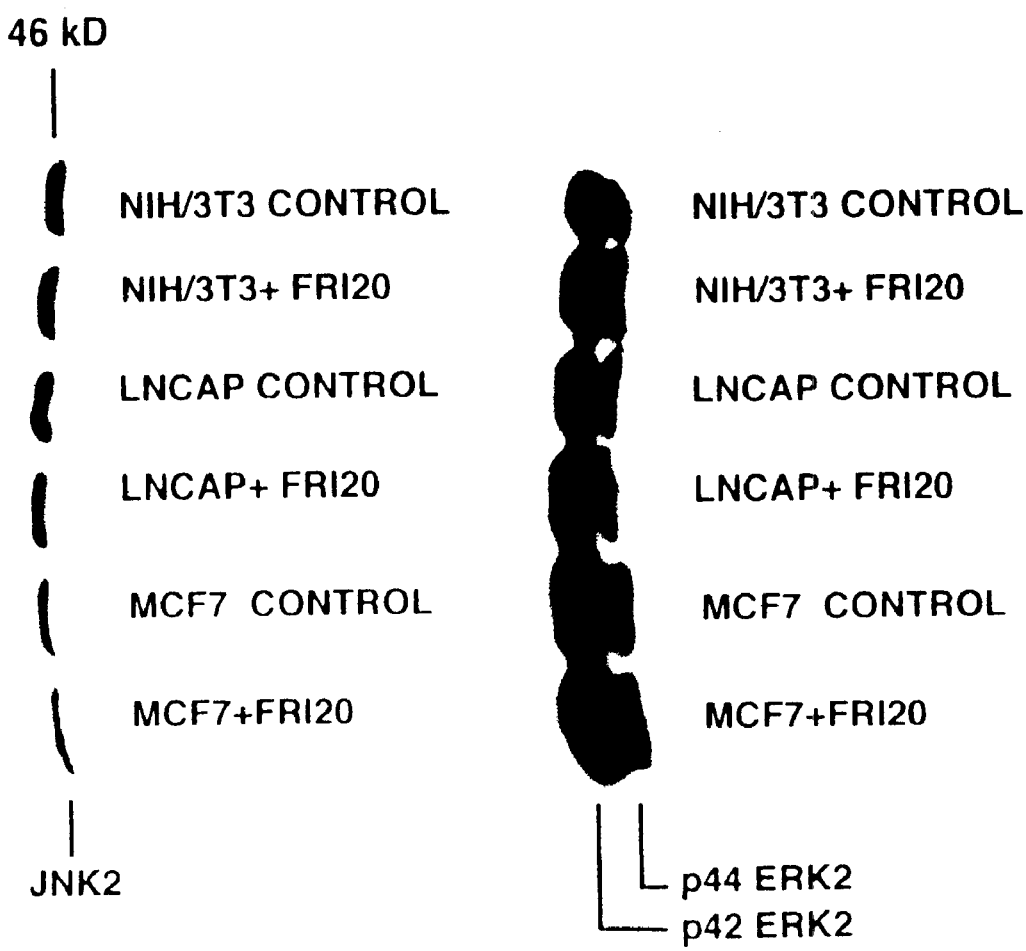
FIG. 6 is blot of the distribution of ERK-2 and JNK/SAPK proteins in NIH3T3, LnCaP and MCF-7 cells. Lysates of cultured cells containing 100 mg of proteins were loaded per lane. Following electrophoresis and transfer to a polyvinylidene membrane, proteins were blotted against ERK-2 and JNK-2 polyclonal antibodies and visualized by chemiluminescence.

Western Blot analysis was carried out on the drug- and mock-treated cell lysates with ERK-2 antibody. Equal amounts of total protein (100 μg) were loaded in each lane of a SDS-PAGE gel (10–12%) and transferred to Immobilon-P (Millipore, USA). Following transfer, membranes were blocked in 3% milk, then probed with ERK-2 and JNK-1 rabbit polyclonal antibodies (Santa Cruz Biotechnology Inc., Santa Cruz, Calif.) and then probed with horseradish peroxidase linked donkey anti-rabbit Ig secondary antibody (Amersham) (1:10000 dilution). The antibody was detected using the ECL Western blotting analysis kit (Amersham) following the manufacturer's instructions. The western blot analysis of the drug- and mock-treated cell lysates with ERK-2 antibody showed the same amount of protein in both lysates (FIG. 6), indicating that higher levels of MBP phosphorylation in mock-treated cells was not due to an unequal quantity of ERK-2 protein in lysates. These results suggest that FRI-20 blocks the phosphorylating capability of ERK-2.

EXAMPLE 32

Effect of FRI-20 on Stress-Activated Protein Activity

To further establish if the activity of stress activated protein kinases (SAPKs), of which JNK is a member, is compromised in the presence of FRI-20, cells (NIH3T3, MCF-7 or LnCaP) were treated with FRI-20 dissolved in DMSO or with DMSO alone. Forty-eight hours later, the cells were lysed with kinase buffer and the lysates used for estimation of the amount of JNK present in each lysate by western blot analysis using JNK polyclonal antibody. The biochemical activity of the JNK present in the FRI-20-treated and mock-treated cell lysates was also determined by immunoprecipitation of JNK followed by incubation with GST-c-Jun protein as a substrate for JNK in the presence of $[\gamma^{-32}P]ATP$.

Accordingly, JNK-1 in 100 mg of cell extracts was immunoprecipitated by incubating the lysate with 1 mg of JNK-1 polyclonal antibody (sc from Santa Cruz Biotechnology) for one hour followed by an additional incubation with 20 μl of protein A-Sepharose (Pharmacia) for one hour. The beads were washed twice with JNK lysis buffer (as described above) followed by two washes with JNK reaction buffer. The beads were resuspended in 40 μl of JNK buffer containing 20 mM $[\gamma^{-32}P]$ ATP (5000 cpm/pmol), and the kinase reaction was carried out for 20 minutes at 30° C. using 3 μg of purified GST-c-Jun(1-79) as substrate. The reaction was stopped, and the radioactivity in the phosphorylated GST-c-Jun protein was quantitated. The results show that the FRI-20 treatment enhanced the ability of JNK to phosphorylate recombinant GST-c-Jun protein by 60–80% compared to mock-treated cells (FIG. 7).

JNK has been shown to be activated by treatment of cells with UV radiation, pro-inflammatory cytokines and environmental stress (Derijard et al., *Cell* 1025 (1994)). The activated JNK binds to the amino terminus of c-jun and increases its transcriptional activity by phosphorylating at ser63 and ser73 (Adler et al., *Proc. Natl. Acad. Sci. USA* 89:5341 (1992); Kwok et al., *Nature* 370:223 (1994)). Without wishing to be bound by any theory, the results demonstrated herein suggest that FRI-20 may act like a pro-inflammatory cytokine or UV light in activating the JNK pathway, which in turn may switch on genes responsible for cell growth inhibition and apoptosis.

EXAMPLE 33

Comparison of FRI-20 and Cisplatin Anti-Tumor Activities

The killing effect of FR-20 on androgen-sensitive (LnCaP) and androgen insensitive (DU145) prostate tumor cells was compared to the effect of cisplatin (cis-diamminedichloroplatinum II), a widely used anti-prostate cancer agent. The cells were grown as in Example 26. FRI-20 or cisplatin was dissolved in DMSO and added to the cells at various concentrations. Viability was determined after 72 hours by the Trypan blue exclusion method. The concentration of FRI-20 required to completely kill LnCaP and DU145 cells was 2.5 μM and 5.0 μM, respectively. Under identical conditions, complete killing of LnCaP and DU145 cells by cisplatin required 25 μM and 15 μM concentrations, respectively. Thus, FRI-20 is at least tenfold more active than cisplatin in killing both hormone-dependent and hormone-independent prostate tumor cells.

EXAMPLE 34

Effect of FRI-6 on Human Carcinoma Cells

Figure 8:
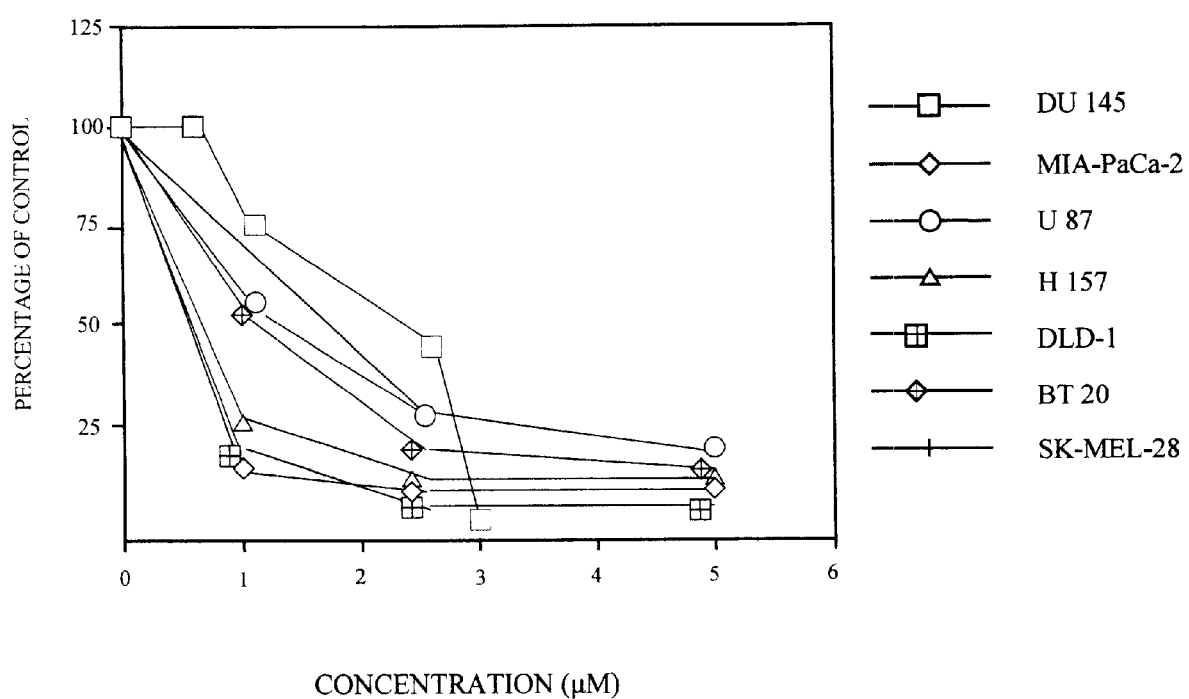
FIG. 8 is a plot of the activity of compound FRI-6 on the human carcinoma cell lines H157 (non-small cell lung), BT20, DLD-1 (colorectal), MIA-PaCa-2 (pancreatic), DU145 (androgen receptor-negative prostate), U87 (glioblastoma) and SK-MEL-28 (melanoma). The cells were treated with various concentrations of FRI-6 24 hours after plating in a total volume of 1 ml of medium using dimethylsulfoxide (DMSO) as a solvent for the compound. Control cells were treated with DMSO alone. The amount of viable cells determined as a percent of the non-treated control group 96 hours after the addition of compound is shown FIG. 8. Cell counts were done in duplicate.

The human carcinoma cell lines listed in Table 5 below were purchased from ATCC and grown in an appropriate growth medium containing 10% fetal bovine serum (FBS) and antibiotics. The cells were plated at a cell density of $1.0 \times 10^5$ cells per 35 mm$^2$ in 6-well dishes. The cells were treated with various concentrations of (E)-fluorostyryl-4-bromobenzylsulfone 24 hours after plating in a total volume of 1 ml of medium using dimethylsulfoxide (DMSO) as a solvent for the compound. Control cells were treated with DMSO alone. The total number of viable cells was determined 96 hours after the addition of the compound by counting the cells in each well using a hemacytometer after trypan blue staining (viable cells exclude the stain). The counts were done in duplicate and the average was graphed in FIG. 8 as a percentage of the non-treated control group. The GI$_{50}$ (the concentration of drug resulting in 50% growth inhibition) was determined for each cell type and listed in Table 5:

TABLE 5

FRI-6 Treatment of Human Carcinoma Cell Lines

| Cell line | Carcinoma type | GI$_{50}$ (μM) |
|---|---|---|
| H157 | lung, non-small cell | <1.0 |
| BT20 | breast, estrogen receptor negative | 1–2 |
| DLD-1 | cob-rectal | <1.0 |
| MIA-PaCa-2 | pancreatic | <1.0 |
| DU145 | prostate, androgen receptor negative | 2.5 |
| U87 | glioblastoma | 1–2 |
| SK-MEL-28 | melanoma | 1–2 |

EXAMPLE 35

Effect of FRI-20 on Human Carcinoma Cells

Applying the same protocol as in Example 34, the GI$_{50}$ for compound FRI-20 treatment of the cell lines in Table 6 was determined:

TABLE 6

FRI-20 Treatment of Human Carcinoma Cell Lines

| Cell line | Carcinoma type | GI$_{50}$ (μM) |
|---|---|---|
| H157 | lung, non-small cell | 1.5 |
| H1299 | lung, non-small cell | 2.0 |
| N417 | lung, small cell | 1.0 |
| H209 | lung, small cell | 1.0 |
| DLD-1 | cob-rectal | 1.0 |
| HCT116 | cob-rectal | 1.0 |
| OvCar-3 | ovarian | 1.5 |
| SK-ov-3 | ovarian | 1.5 |
| CAKI-1 | renal | 1.5 |
| CAKI-2 | renal | 1.0 |
| U87 | glioblastoma | 2.0 |

TABLE 6-continued

FRI-20 Treatment of Human Carcinoma Cell Lines

| Cell line | Carcinoma type | GI$_{50}$ ($\mu$M) |
|---|---|---|
| H80 | glioblastoma | 1.5 |
| SW1088 | astrocytoma | 2.0 |
| Raji | Burkets lymphoma | 2.0 |
| Daudi | Burkets lymphoma | 2.0 |
| CEM | acute lymphocytic lymphoma | 1.0 |
| A431 | epidermoid | 0.8 |
| MIA-PaCa-2 | pancreatic | 0.5 |
| BxPC-3 | pancreatic | 0.5 |
| SK-MEL-3 | melanoma | 2.0 |
| SK-MEL-28 | melanoma | 2.0 |
| MES-SA | uterine sarcoma | 1.0 |
| Hs 416.T | squamous papilloma | 4.0 |
| Hs-802.T | squamous cell carcinoma | 4.0 |
| TE 354 | basal cell carcinoma | 4.0 |
| Detroit 525 | Turner Syndrome skin fibroblast | 3.0 |
| Hs 456.BT | benign skin lesion | 3.0 |

EXAMPLE 36

E-(2)-chloro-4-fluorostyryl-4-chlorobenzylsulfone

A solution of 4-chlorobenzylsulfonyl acetic acid (0.01 mol) and 2-chloro-4-fluorobenzaldehyde (0.01 mol) was subjected to Procedure 1. The title compound was obtained in 66% yield, melting point 149–150° C.

EXAMPLE 37

Effect of (E)-2-Chloro-4-Fluorostyryl-4-Chlorobenzylsulfone on Human Carcinoma Cells Applying the same protocol as in Example 34, the GI$_{50}$ for (E)-2-chloro-4-fluorostyryl-4-chlorobenzylsulfone treatment of the cell lines in Table 7 was determined:

TABLE 7

(E)-2-Chloro-4-fluorostyryl-4-chlorobenzylsulfone
Treatment of Human Carcinoma Cell Lines

| Cell line | Carcinoma type | GI$_{50}$ ($\mu$M) |
|---|---|---|
| H157 | lung, non-small cell | 1.5 |
| DLD-1 | cob-rectal | 0.8 |
| U87 | glioblastoma | 1.8 |
| MIA-PaCa-2 | pancreatic | 1.0 |
| DU-145 | prostate | 2.0 |
| BT20 | breast | 0.9 |

The data demonstrate that the styryl sulfone compounds are active against tumor cells representing a broad range of tissues. In particular, the compounds are active not only against highly tumorigenic cell lines such as the breast tumor cell line BT20, but also against less tumorigenic lines and even non-tumorigenic hyperplasias such as Turner Syndrome fibroblasts and benign skin lesions.

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indication the scope of the invention.

What is claimed is:

1. A method of treating an individual for a cancer other than prostate or breast cancer comprising administering to said individual an effective amount of a compound of formula II

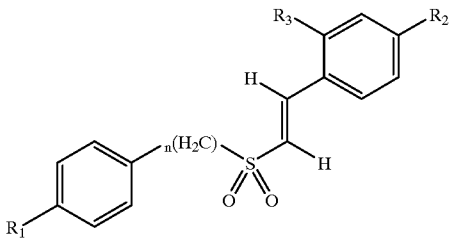

wherein
n is zero or one;
R$_1$ is selected from the group consisting of hydrogen, chlorine, fluorine and bromine;
R$_2$ is selected from the group consisting of hydrogen, chlorine, fluorine, bromine, methyl and methoxy; and
R$_3$ is selected from the group consisting of hydrogen, chlorine and fluorine; provided,
R$_2$ may not be methyl or methoxy when R$_1$ and R$_3$ are both hydrogen and n is zero or one; and
R$_1$, R$_2$ and R$_3$ may not all be hydrogen when n is one.

2. The method according to claim 1 wherein the compound is E-4-bromostyryl phenyl sulfone.

3. The method according to claim 1 wherein the compound is E-2,4-difluorostyryl 4-fluorobenzyl sulfone.

4. The method according to claim 1 wherein the compound is E-2-chloro-4-fluorostyryl 4-chlorobenzyl sulfone.

5. The method according to claim 1, wherein R$_3$ is hydrogen, and R$_1$ and R$_2$ are independently selected from the group consisting of chlorine, fluorine and bromine.

6. The method according to claim 5 wherein the compound is E-4-chlorostyryl 4-chlorophenyl sulfone.

7. The method according to claim 5 wherein the compound is E-4-bromostyryl 4-chlorophenyl sulfone.

8. The method according to claim 5 wherein the compound is E-4-fluorostyryl 4-chlorobenzyl sulfone.

9. The method according to claim 5 wherein the compound is E-4-chlorostyryl 4-chlorobenzyl sulfone.

10. The method according to claim 5 wherein the compound is E-4-fluorostyryl 4-fluorobenzyl sulfone.

11. The method according to claim 5 wherein the compound is E-4-fluorostyryl 4-bromobenzyl sulfone.

12. The method according to claim 5 wherein the compound is E-4-bromostyryl 4-bromobenzyl sulfone.

13. The method according to claim 5 wherein the compound is E-4-bromostyryl 4-fluorobenzyl sulfone.

14. The method according to claim 5 wherein the compound is E-4-chlorostyryl 4-bromobenzyl sulfone.

15. The method according to claim 5 wherein the compound is E-4-bromostyryl 4-chlorobenzyl sulfone.

16. The method according to claim 1 wherein the cancer is selected from the group consisting of cancers of the ovaries, lung, colon, rectum, brain, kidney, pancreas and skin; leukemias; lymphomas; sarcomas; squamous cell carcinomas and papillomas; basal cell carcinomas and papillomas; and epidermoid cancers.

17. The method according to claim 16 wherein the compound is selected from the group consisting of (E)-4-fluorostyryl-4-chlorobenzyl sulfone, (E)-4-fluorostyryl-4-bromobenzyl sulfone, (E)-4-chlorostyryl-4-bromobenzyl sulfone and (E)-2-chloro-4-fluorostyryl-4-chlorobenzyl sulfone.

18. A method of inhibiting the growth of tumor cells in an individual afflicted with cancer, other than breast or prostate tumor cells, comprising administering to said individual an effective amount of a compound of formula II

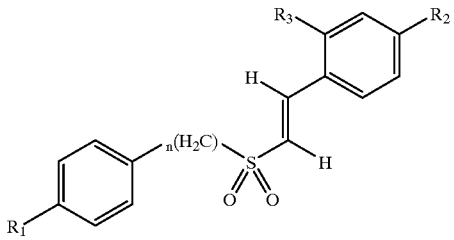

wherein n is zero or one;

$R_1$ is selected from the group consisting of hydrogen, chlorine, fluorine and bromine;

$R_2$ is selected from the group consisting of hydrogen, chlorine, fluorine, bromine, methyl and methoxy; and $R_3$ is selected from the group consisting of hydrogen, chlorine and fluorine; provided, $R_2$ may not be methyl or methoxy when $R_1$ and $R_3$ are both hydrogen and n is zero or one; and $R_1$, $R_2$ and $R_3$ may not all be hydrogen when n is one.

19. A method according to claim 18 wherein the inhibition of growth of said tumor cells includes inducing apoptosis of tumor cells.

20. A method of treating an individual for a cancer other than prostate or breast cancer comprising administering to said individual an effective amount of a compound of formula III

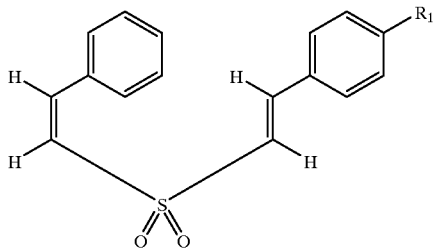

wherein $R_1$ is selected from the group consisting of hydrogen, chlorine, fluorine and bromine.

21. The method according to claim 20 wherein the cancer is selected from the group consisting of cancers of the ovaries, lung, colon, rectum, brain, kidney, pancreas and skin; leukemias; lymphomas; sarcomas; squamous cell carcinomas and papillomas; basal cell carcinomas and papillomas; and epidermoid cancers.

22. A method of inhibiting the growth of tumor cells in an individual afflicted with cancer, other than breast or prostate tumor cells, comprising administering to said individual an effective amount of a compound of formula III

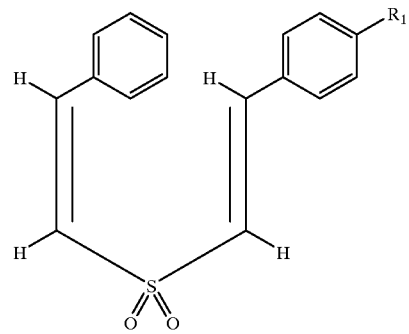

wherein $R_1$ is selected from the group consisting of hydrogen, chlorine, fluorine and bromine.

23. A method according to claim 22 wherein the inhibition of growth of said tumor cells includes inducing apoptosis of tumor cells.

24. A method of treating an individual for a cancer other than prostate or breast cancer comprising administering to said individual an effective amount of a compound of formula IV

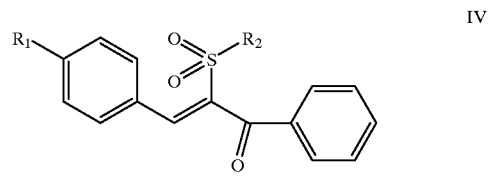

wherein $R_1$ is selected from the group consisting of fluorine and bromine, and $R_2$ is selected from the group consisting of 2-chlorophenyl, 4-chlorophenyl, 4-fluorophenyl and 2-nitrophenyl.

25. The method according to claim 24 wherein the cancer is selected from the group consisting of cancers of the ovaries, lung, colon, rectum, brain, kidney, pancreas and skin; leukemias; lymphomas; sarcomas; squamous cell carcinomas and papillomas; basal cell carcinomas and papillomas; and epidermoid cancers.

26. A method of inhibiting the growth of tumor cells in an individual afflicted with cancer, other than breast or prostate tumor cells, comprising administering to said individual an effective amount of a compound of formula IV

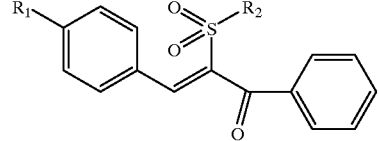

wherein $R_1$ is selected from the group consisting of fluorine and bromine, and $R_2$ is selected from the group consisting of 2-chlorophenyl, 4-chlorophenyl, 4-fluorophenyl and 2-nitrophenyl.

27. A method according to claim 26 wherein the inhibition of growth of said tumor cells includes inducing apoptosis of tumor cells.

* * * * *